(12) United States Patent
Lyle et al.

(10) Patent No.: US 10,771,410 B2
(45) Date of Patent: Sep. 8, 2020

(54) DEVICES, SYSTEMS AND METHODS FOR SUPPORTING A VETERINARY PRACTICE

(71) Applicant: Zoetis Services LLC, Florham Park, NJ (US)

(72) Inventors: Scott Devon Lyle, London (GB); Daniel Charles Smith, London (GB)

(73) Assignee: Zoetis Services LLC, Parsippany, NJ (US)

( * ) Notice: Subject to any disclaimer, the term of this patent is extended or adjusted under 35 U.S.C. 154(b) by 936 days.

(21) Appl. No.: 14/679,161

(22) Filed: Apr. 6, 2015

(65) Prior Publication Data

US 2015/0294072 A1 Oct. 15, 2015

Related U.S. Application Data

(60) Provisional application No. 61/977,963, filed on Apr. 10, 2014.

(51) Int. Cl.
| | |
|---|---|
| *H04L 12/58* | (2006.01) |
| *G06F 3/0481* | (2013.01) |
| *G06F 3/0484* | (2013.01) |
| *G16H 10/60* | (2018.01) |
| *G16H 40/20* | (2018.01) |
| *G06F 19/00* | (2018.01) |

(52) U.S. Cl.
CPC .......... *H04L 51/046* (2013.01); *G06F 3/0484* (2013.01); *G06F 3/04817* (2013.01); *G16H 10/60* (2018.01); *G16H 40/20* (2018.01); *G06F 19/3456* (2013.01); *G06F 19/3481* (2013.01)

(58) Field of Classification Search
CPC .... G06Q 50/22; G06Q 50/24; G06Q 3/04817; G06Q 3/0484; G06F 3/04817; G06F 3/0484; G06F 19/3418; G06F 19/3456; G16H 10/60; G16H 40/20; H04L 51/046
USPC ........................................... 705/2-3
See application file for complete search history.

(56) References Cited

U.S. PATENT DOCUMENTS

| | | |
|---|---|---|
| 6,208,974 B1 | 3/2001 | Campbell et al. |
| 6,397,190 B1 | 5/2002 | Goetz |
| 6,621,508 B1 * | 9/2003 | Shiraishi ............... G06F 3/0481 715/764 |
| 6,910,050 B2 | 6/2005 | Pawlick |
| 8,452,670 B2 | 5/2013 | Sutter et al. |

(Continued)

FOREIGN PATENT DOCUMENTS

| | | |
|---|---|---|
| CA | 2226612 A1 | 4/1999 |
| WO | WO 2005/043431 A2 | 5/2005 |

(Continued)

OTHER PUBLICATIONS

PCT International Search Report and Written Opinion, International Application No. PCT/US2015/024922, dated Jul. 2, 2015.

*Primary Examiner* — Joy Chng
(74) *Attorney, Agent, or Firm* — Scott C. Mayhew

(57) ABSTRACT

Systems and techniques for supporting a veterinary practice are provided. Further, systems and techniques for the collection and display of animal wellness information are provided. Animal wellness data relating to a single animal patient or group of animal patients are collected and subsequently displayed at a desired remote location or on a mobile device so that a veterinarian can review the information.

5 Claims, 28 Drawing Sheets

(56) References Cited

U.S. PATENT DOCUMENTS

| | | |
|---|---|---|
| 8,799,015 B2 | 8/2014 | Goodnight et al. |
| 2003/0136834 A1 | 7/2003 | Scheurer |
| 2003/0204417 A1 | 10/2003 | Mize |
| 2003/0212574 A1 | 11/2003 | Olivier |
| 2004/0199412 A1 | 10/2004 | McCauley |
| 2005/0027580 A1 | 2/2005 | Crici et al. |
| 2005/0065822 A1* | 3/2005 | Ying ............... G16H 30/20 705/3 |
| 2005/0108052 A1 | 5/2005 | Omaboe |
| 2005/0261959 A1 | 11/2005 | Moyer |
| 2006/0074718 A1 | 4/2006 | Fucci et al. |
| 2006/0260557 A1 | 11/2006 | McCabe et al. |
| 2007/0077551 A1* | 4/2007 | Hirayama ........ G01N 35/00584 435/4 |
| 2007/0265882 A1 | 11/2007 | Jennings et al. |
| 2008/0059294 A1 | 3/2008 | Schauser et al. |
| 2008/0086328 A1* | 4/2008 | Hertel ............... G06Q 50/22 705/2 |
| 2009/0106044 A1 | 4/2009 | Schweisguth et al. |
| 2009/0138310 A1 | 5/2009 | Beall |
| 2009/0182586 A1 | 7/2009 | Cohane |
| 2011/0054978 A1 | 3/2011 | Mohil |
| 2011/0077958 A1 | 3/2011 | Breitenstein et al. |
| 2012/0078660 A1 | 3/2012 | Mangicaro et al. |
| 2012/0203678 A1 | 8/2012 | Sutter et al. |
| 2012/0265702 A1 | 10/2012 | Maher |
| 2013/0073554 A1 | 3/2013 | Bachert et al. |
| 2013/0096937 A1 | 4/2013 | Campbell et al. |
| 2013/0138458 A1 | 5/2013 | Lorsch |
| 2013/0173439 A1 | 7/2013 | Christiansen |
| 2013/0218592 A1 | 8/2013 | Hashmat |
| 2014/0006055 A1 | 1/2014 | Seraly et al. |
| 2014/0077932 A1* | 3/2014 | Rooyakkers ........... G06Q 10/00 340/7.51 |
| 2014/0142973 A1 | 5/2014 | Henley |
| 2014/0244280 A1 | 8/2014 | Fitz |
| 2014/0267299 A1 | 9/2014 | Couse |
| 2014/0275824 A1* | 9/2014 | Couse ............... A61B 5/1112 600/301 |

FOREIGN PATENT DOCUMENTS

| | | |
|---|---|---|
| WO | WO 2007/129917 A1 | 11/2007 |
| WO | WO 2012/065031 A2 | 5/2012 |
| WO | WO 2014/028680 A1 | 2/2014 |

* cited by examiner

Vaccination Reminder & Annual Health Check

Animal House Veterinary Centre
www.animalhouse.co.uk
Tel: 01383 850 530

Dear Mr John Toole

Your pet Ralph is due their annual health check. Vaccination is a vital part of this check up to maintain protection against many potentially fatal and infectious diseases. We all know that our pets age much faster than we do, which is why this annual health check plays such an essential part in keeping your pet healthy.

> Call us now to arrange a vaccination and annual health check appointment on 01 383 850 530.

Visiting Your Vet

00:00 — 03:36

Animal House Veterinary Centre

Privacy Notice: OST Village Vets respects your privacy. "Vaccination Reminder" is privacy controlled and distributed by OST Village Vets. We never release your email address to third parties. To unsubscribe from future "Vaccination Reminders" mailings: click here.

FIG. 33

E-Room
Call Me Back Request

Name:
Mickey Mouse
Pet Name:
Daffy Duck
Phone:
07825543583
Callback Time:
Morning

← → ⟳ 🏠 | http://performanceindex.z.com |

Performance Index

Dashboard  Reports  Manage Practice

Benchmark
Geography
( ) National
( ) Regional
Location
( ) Urban
( ) Rural
Practice Size
( ) <10 FTE
( ) 11-20 FTE
( ) 20-50 FTE
( ) 50+ FTE

[Apply]

Edit KPIs

| ▽ | ▽ Growth:Actual | ▽ Growth % | ▽ Actual Value |
|---|---|---|---|
| KPI | % | % | # |
| KPI | % | % | # |
| KPI | % | % | # |

| ▽ | ▽ Growth:Actual | ▽ Growth % | ▽ Actual Value |
|---|---|---|---|
| KPI | % | % | # |
| KPI | % | % | # |
| KPI | % | % | # |

| ▽ | ▽ Growth:Actual | ▽ Growth % | ▽ Actual Value |
|---|---|---|---|
| KPI | % | % | # |
| KPI | % | % | # |
| KPI | % | % | # |

250

FIG. 37 http://performanceindex.z.com

Performance Index

Dashboard  Practice Overview  Manage Practice

Manage Practice

Practice Name:   Smith Veterinary Practice
Address:         123 High St
                 Ste 214
                 Kensington, London, UK 72H-02
Phone:           +44 01 23 45 67 89
Alt Phone:       +44 01 23 45 67 89

Location:        ○ Rural   ⊙ Urban

Total Number of FTEs: ☐—320
                      Explanation of what FTE means.
Number of FTE Vets:   ☐—320

Number of Operating Theatres: ☐⎫
Number of Consult Rooms:      ☐⎬—320
Percentage Profit Last Year:  ☐⎭

Goals

Net Profit Percentage Target: ☐—320
Annual Turnover Target:       ☐—320

FIG. 38

DEVICES, SYSTEMS AND METHODS FOR SUPPORTING A VETERINARY PRACTICE

CROSS REFERENCE TO RELATED APPLICATION

This application claims the benefit of U.S. Provisional Patent Application No. 61/977,963, filed Apr. 10, 2014, which is expressly incorporated herein by reference in its entirety.

TECHNICAL FIELD

The present disclosure generally relates to the collection and display of information for supporting a veterinary practice. More particularly, the present disclosure relates to the collection of animal wellness information and data over a network, and displaying the collected information.

BACKGROUND

Remote monitoring of animal patients enables veterinarians to track wellness information over time such that the veterinarian can identify issues that may not be evident when the animal visits the veterinarian's office. Accordingly, it would be desirable to provide improved systems and methods for collecting and displaying animal wellness information for a plurality of animal patients to veterinarian professionals. Such systems and methods may also desirably provide improved means for efficiently operating a veterinary practice.

BRIEF SUMMARY

The above and other needs are met by aspects of the present disclosure which, according to one aspect, provides a digital web portal for supporting a veterinary practice. The digital web portal includes a processor and a display device in communication with the processor and having a graphical user interface. A plurality of acuatable icons are displayed on the graphical user interface. The actuatable icons are associated with a plurality of business-related functions for operating a veterinary practice, with each icon being actuatable to access an associated portlet and display additional information associated with the respective function of a veterinary practice on the graphical user interface.

Thus, various aspects of the present disclosure provide advantages, as otherwise detailed herein.

BRIEF DESCRIPTION OF THE DRAWINGS

Figure 1:
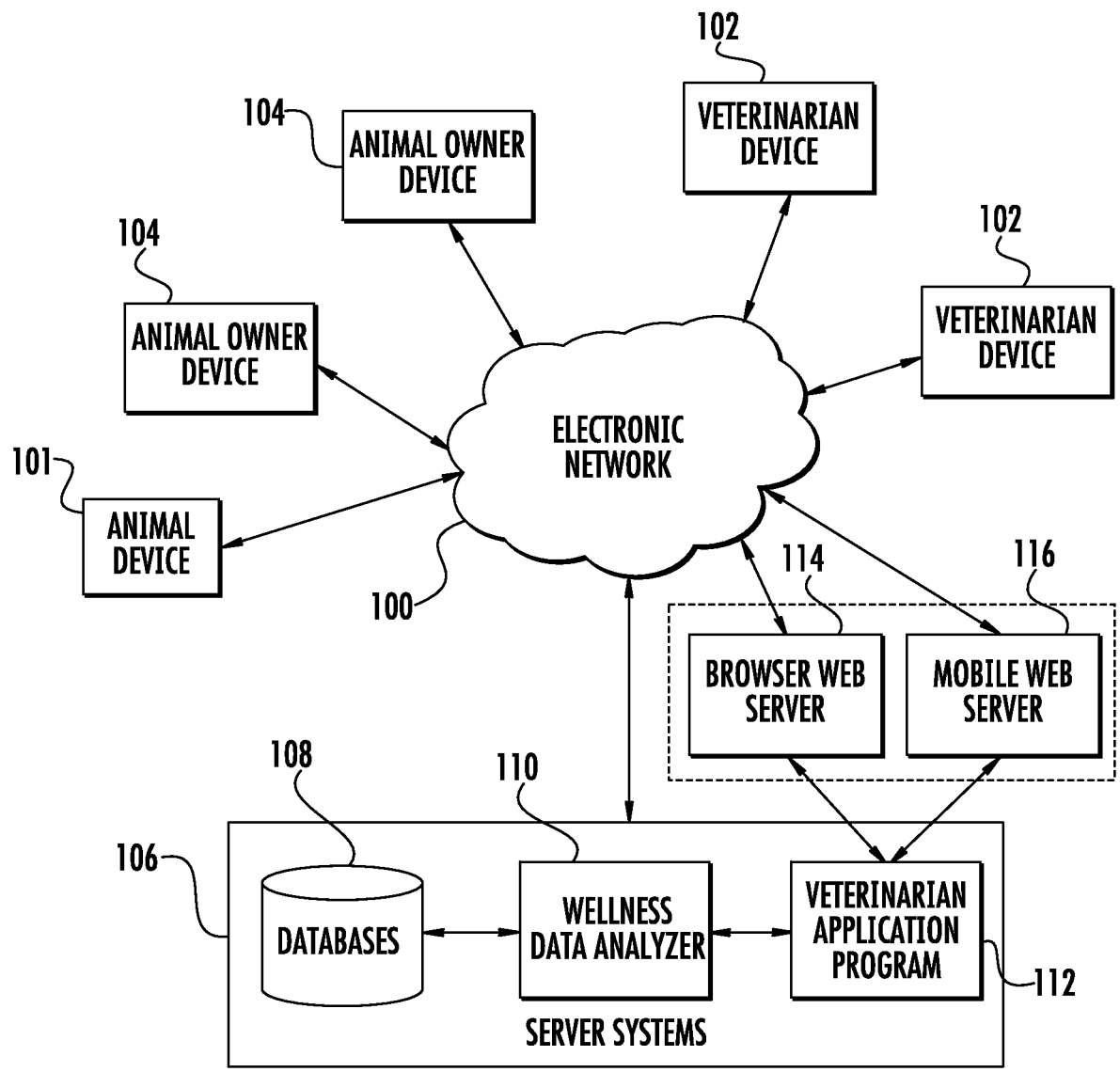
Figure 2:
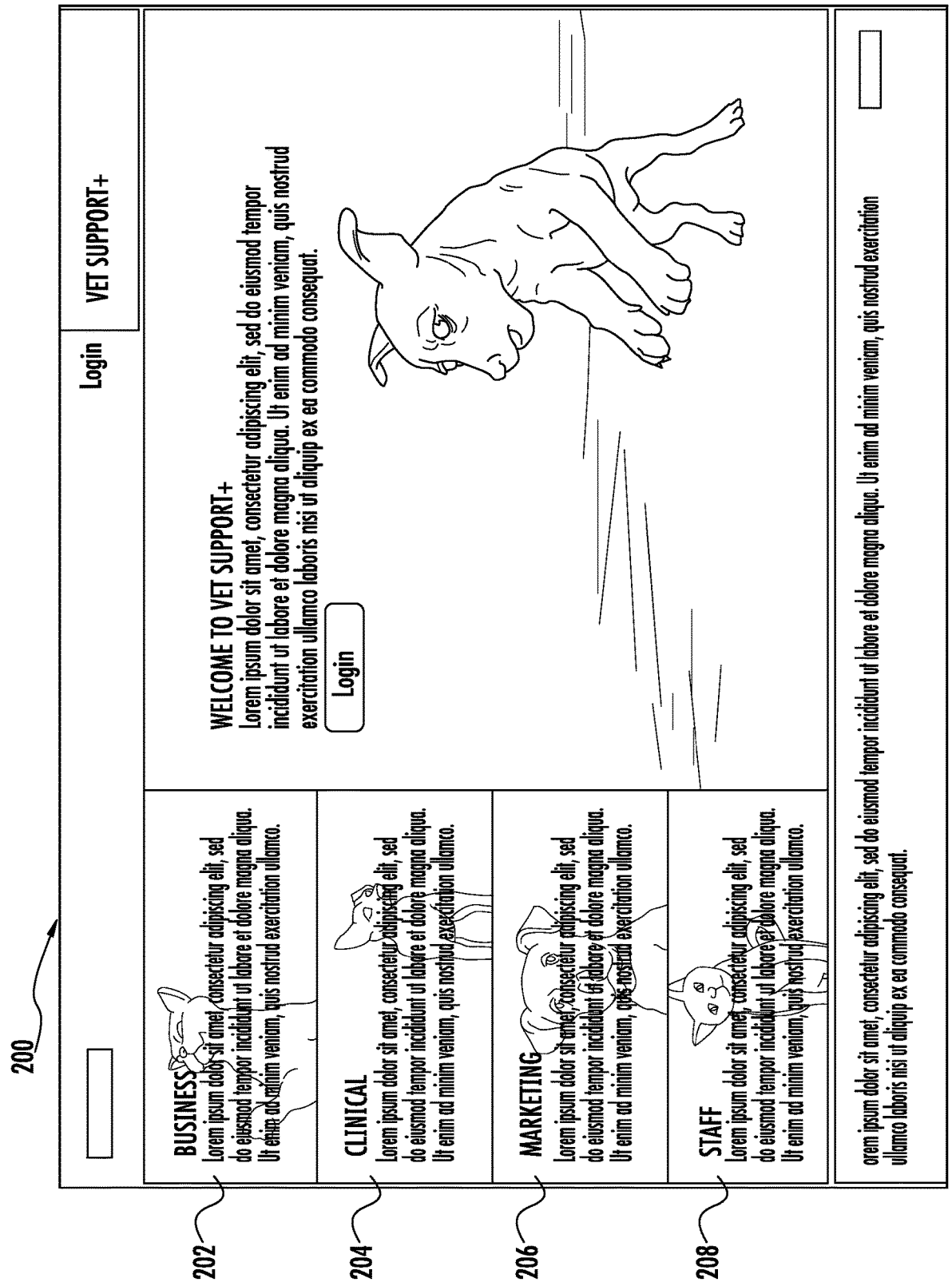
Figure 3:
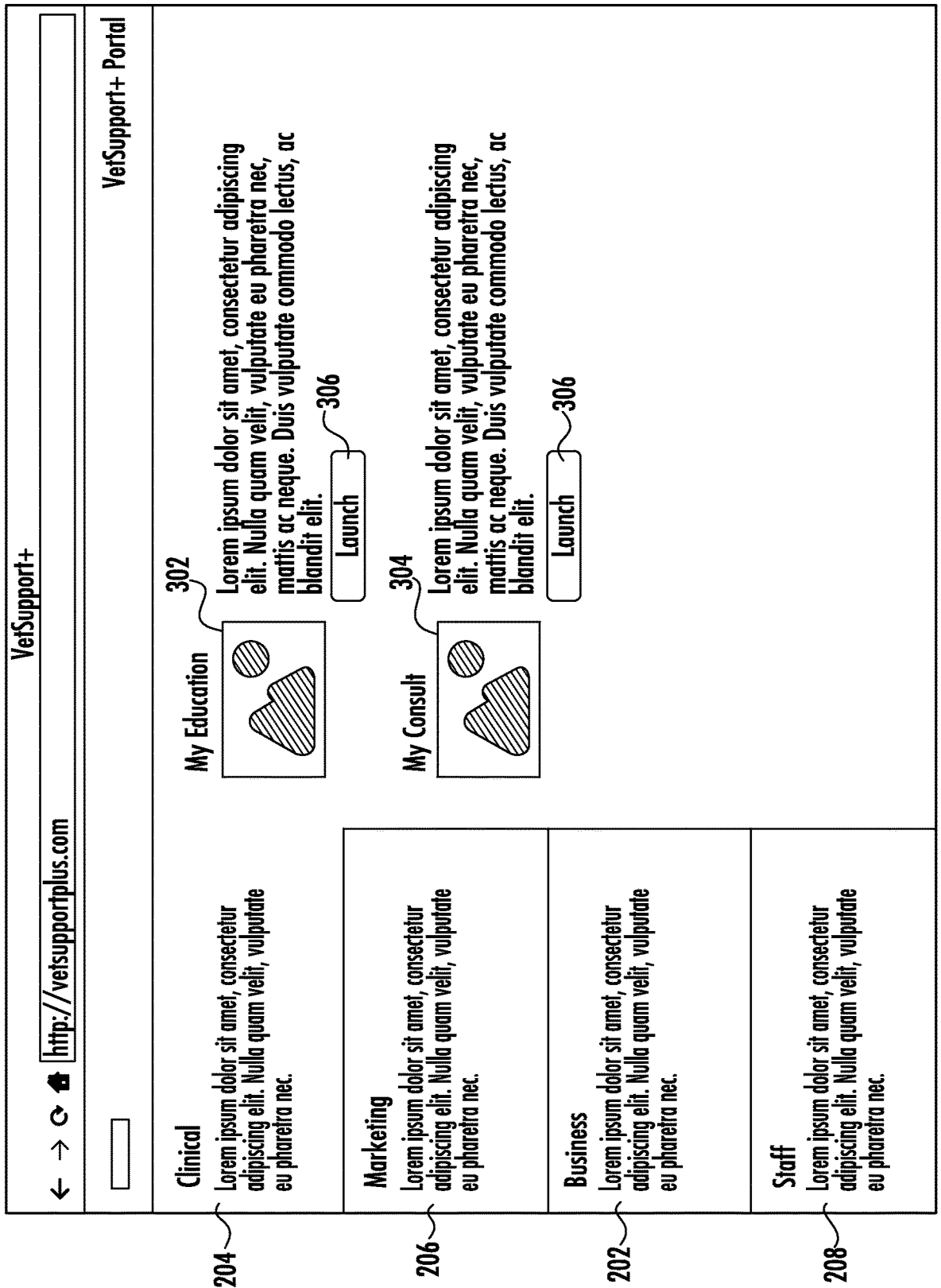
Figure 13:
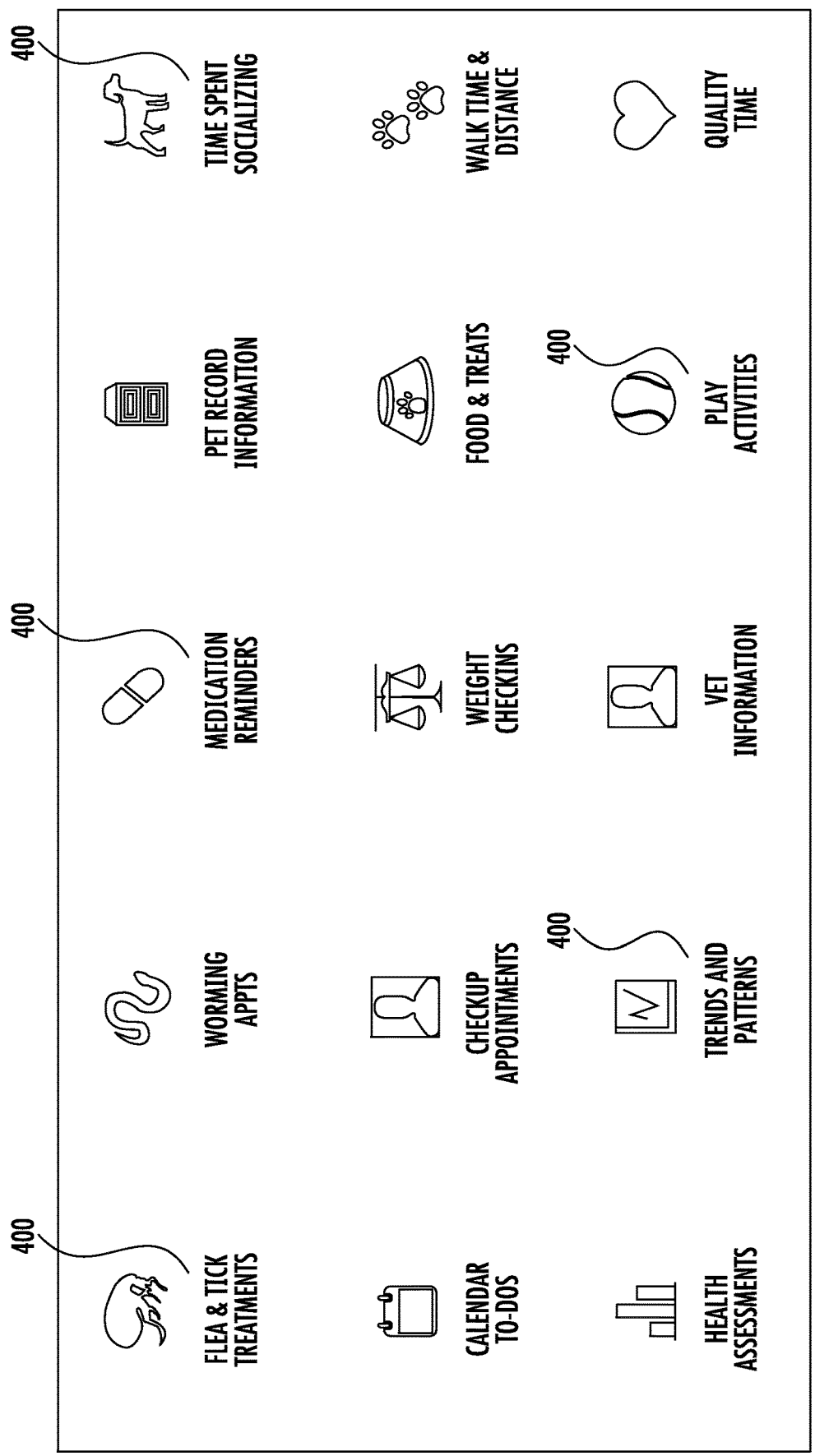
Figure 30:
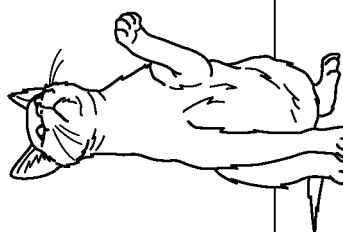
Figure 31:
Figure 32:
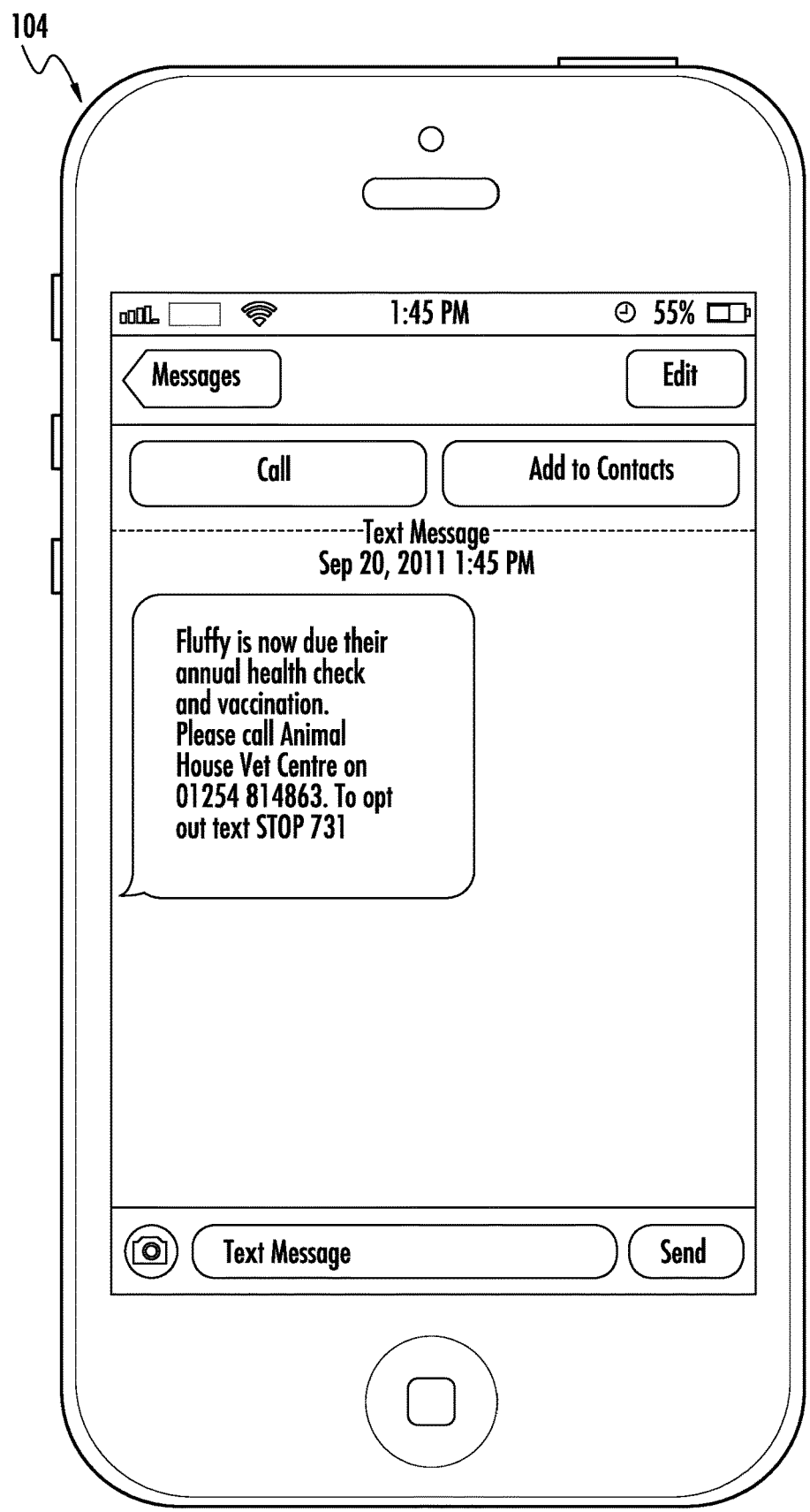
Figure 36:
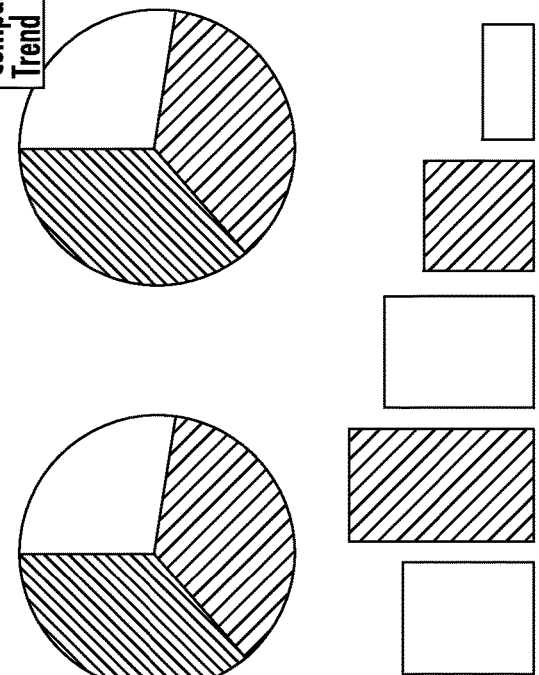

Having thus described various embodiments of the present disclosure in general terms, reference will now be made to the accompanying drawings, which are not necessarily drawn to scale, and wherein:

FIG. 1 is a schematic diagram of a system and environment for collecting, processing, and displaying information for supporting a veterinary practice, according to one aspect of the present disclosure;

FIG. 2 is a screenshot of a veterinarian interface for reviewing information related to a veterinary practice, according to one aspect of the present disclosure;

FIG. 3 is a wireframe of a veterinarian interface for reviewing information related to a veterinary practice, according to one aspect of the present disclosure;

FIGS. 4-12 are screenshots of a veterinarian interface for reviewing information related to a veterinary practice, according to various aspects of the present disclosure;

FIG. 13 is a schematic view of a plurality of actuatable icons for a mobile application capable of providing animal wellness information to a veterinary practice support system;

FIGS. 14-29 are screenshots of an animal owner device capable of inputting information related to wellness data of a subject animal, according to various aspects of the present disclosure;

FIG. 30 is a screenshot of a veterinarian interface for reviewing information related to a veterinary practice, according to one aspect of the present disclosure;

FIG. 31 is a screenshot of a veterinarian interface for reviewing information related to a veterinary practice, according to one aspect of the present disclosure;

FIG. 32 is an image of an animal owner device depicting a screenshot showing information received from a veterinary practice support system, according to one aspect of the present disclosure;

FIG. 33 is a screenshot of an animal owner device capable of receiving information from a veterinary practice support system, according to one aspect of the present disclosure;

FIG. 34 is a screenshot of a veterinarian interface for reviewing information related to a veterinary practice, according to one aspect of the present disclosure;

FIGS. 35-37 are wireframes of a veterinarian interface for reviewing information related to a veterinary practice, according to various aspects of the present disclosure; and FIG. 38 is a screenshot of a veterinarian interface for reviewing information related to a veterinary practice, according to one aspect of the present disclosure.

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

The methods, systems and devices provided herein may be implemented to deliver a portfolio of e-products and digital solutions to assist veterinarians improve medical value to their animal patients, grown their client base and increase productivity. According to some aspects, a web portal may be implemented to provide such digital solutions to a veterinarian for efficiently operating a veterinary practice.

A veterinary practice support system may include a processor controlled by instructions stored in a memory. For example, the transceiver assembly may include and be controlled by such a processor, and the remote server may be controlled by another such processor. The memory may be random access memory (RAM), read-only memory (ROM), flash memory or any other memory, or combination thereof, suitable for storing control software or other instructions and data.

Some of the functions performed by the veterinary practice support system are described with reference to flowcharts and/or block diagrams. Those skilled in the art should readily appreciate that functions, operations, decisions, etc.

of all or a portion of each block, or a combination of blocks, of the flowcharts or block diagrams may be implemented as computer program instructions, software, hardware, firmware or combinations thereof.

Those skilled in the art should also readily appreciate that instructions or programs defining the functions of the present disclosure may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer network. Further, the instructions or programs may be provided as or otherwise with a non-transitory computer readable medium, which includes a hard drive, compact disk, flash memory, volatile memory, etc., but does not include a transitory signal per se.

In addition, while the disclosure may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

Exemplary aspects of a veterinary practice support system will now be described with reference to the screenshots depicted in FIGS. 2-11, 30, 31 and 35-38. It will be appreciated that the screenshots are only exemplary, and that any desired user interface, touch interface mobile application, user elements, or manipulatable icons or shapes may be used to execute the disclosed methods. FIG. 1 is a schematic diagram of a system and environment for supporting a veterinary practice, according to an exemplary aspect of the present disclosure. As shown in FIG. 1, the system and environment may include one or more veterinarian devices 102 capable of being disposed in communication with an electronic network 100. Electronic network 100 may be the Internet, or any other combination of wired and/or wireless electronic networks.

In one aspect, each of veterinarian devices 102 may include a server, personal computer, tablet computer, mobile device, smartphone, and/or personal digital assistant ("PDA") disposed in communication with electronic network 100. For example, in one embodiment, each of veterinarian devices 102 may be a touchscreen enabled device, such as an Apple iPad, Samsung Galaxy, Amazon Kindle, Microsoft Surface, or any other equivalent or similar device. Each of veterinarian devices 102 may have a web browser or mobile browser installed for receiving and displaying content from web servers. Thus, each of veterinarian devices 102 may be configured to receive and display data that is received, such as from animal owners, and processed, over electronic network 100.

FIG. 2 is a screenshot of a veterinarian interface (e.g., a graphical user interface (GUI)) for logging into a web portal for supporting a veterinary practice. The log-in interface 200 may appropriately limit access to data and information specific to the veterinary practice. The log-in interface may have background images or other indicia, which may be customizable. In some instances, the log-in interface may also display a series of actuatable icons, such as, for example, a business category icon 202, a clinical category icon 204, a marketing category icon 206, and a staff category icon 208, each representing a primary category associated with the veterinary practice. Each icon may be actuatable to access an associated portlet and display additional information associated with the respective category or area (e.g., clinical, marketing, business and staff) of a veterinary practice on the veterinarian interface. Each icon or proximate thereto may include visual and/or textual indicia for providing information about each primary category.

FIG. 3 is a wireframe of a veterinarian interface as displayed once the veterinarian has logged-in to the web portal. In this particular instance, the veterinarian has selected or otherwise actuated the clinical icon 204. Such a selection may provide the veterinarian with one or more actuatable icons representing secondary selections or sub-selections within the primary category. For example, the clinical portlet may offer an educational module and a consultation module as represented by an educational indicia 302 and a consultation indicia 304, respectively. The veterinarian may be provided with one or more launch icons 306 to access the desired module. According to some aspects, the business portlet may offer a rebate module and a practice support module; the marketing portlet may offer a mobile application module and a communications module; and the staff portlet may offer a human resources (HR) module and a reporting module.

Figure 4:
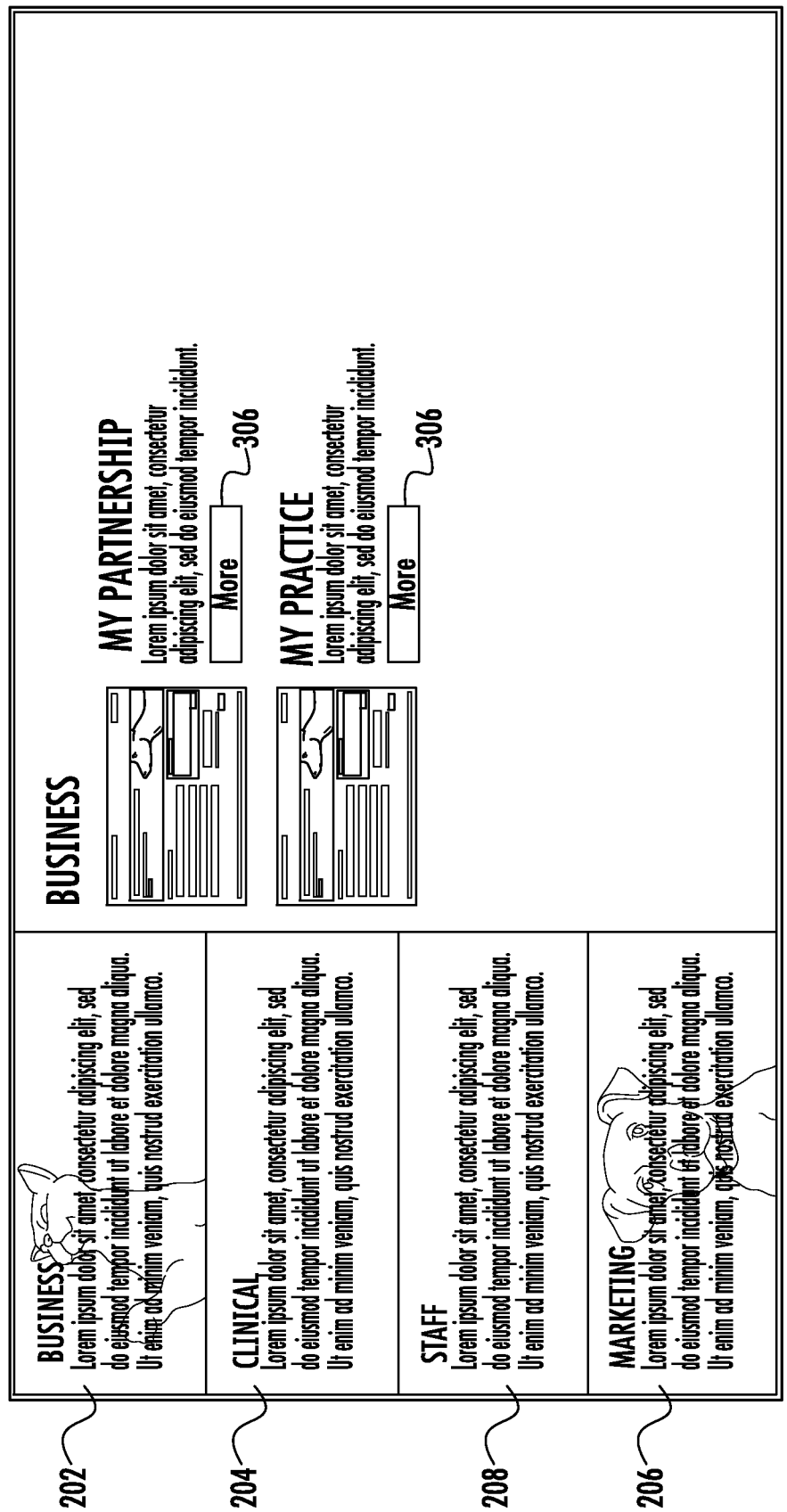
Figure 5:
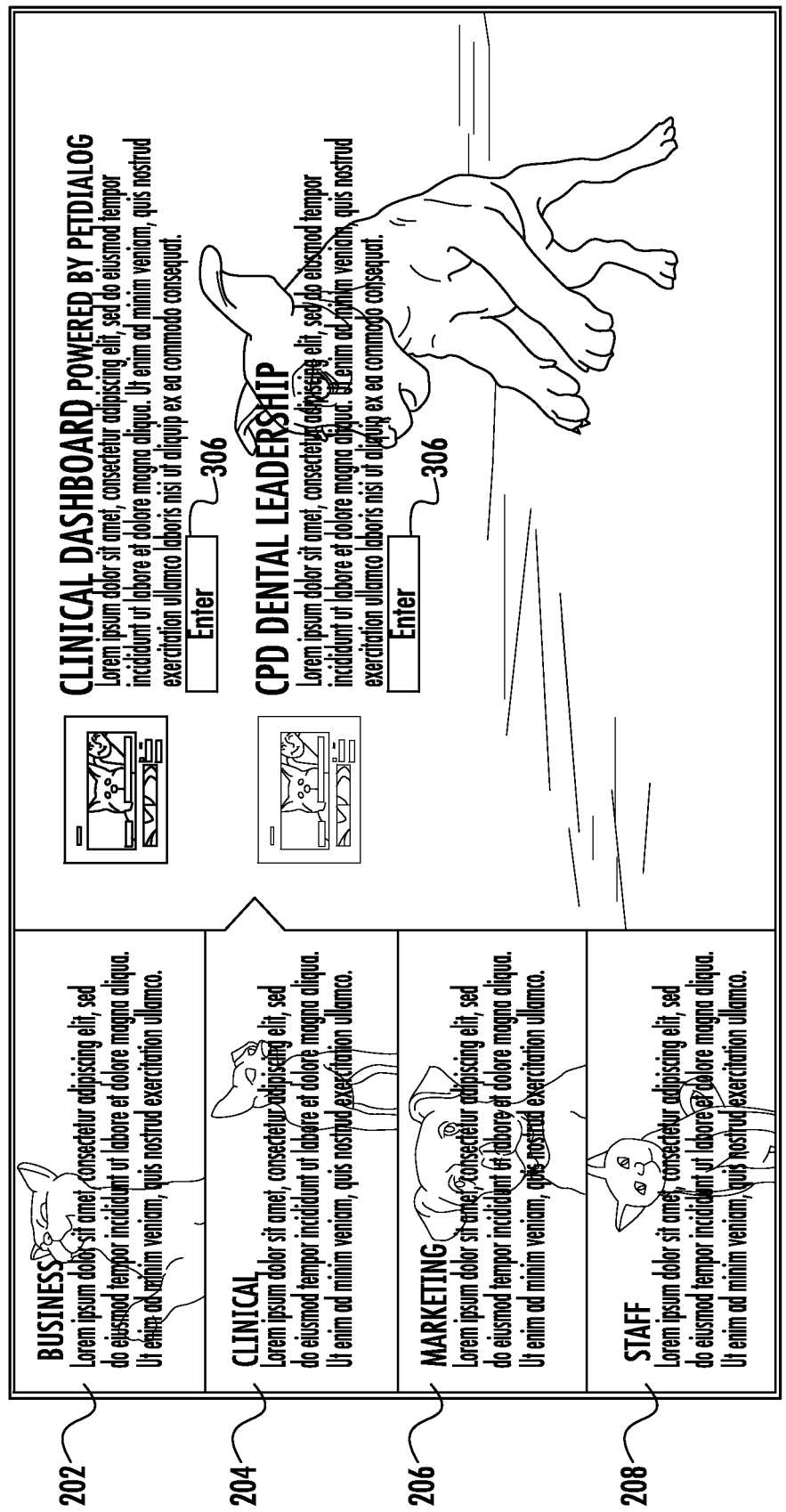

As shown in FIGS. 4 and 5, the veterinarian interface may highlight or otherwise visually distinguish the selected icon such that the remaining icons are indicated as unselected. For example, FIG. 4 illustrates the business portlet as the selected primary category, while FIG. 5 illustrates the clinical portlet as the selected primary category. FIG. 4 illustrates the modules available to be accessed as sub-categories of the business category, while FIG. 5 illustrates the modules available to be accessed as sub-categories of the clinical category (a dashboard module and a leadership module).

Figure 6:
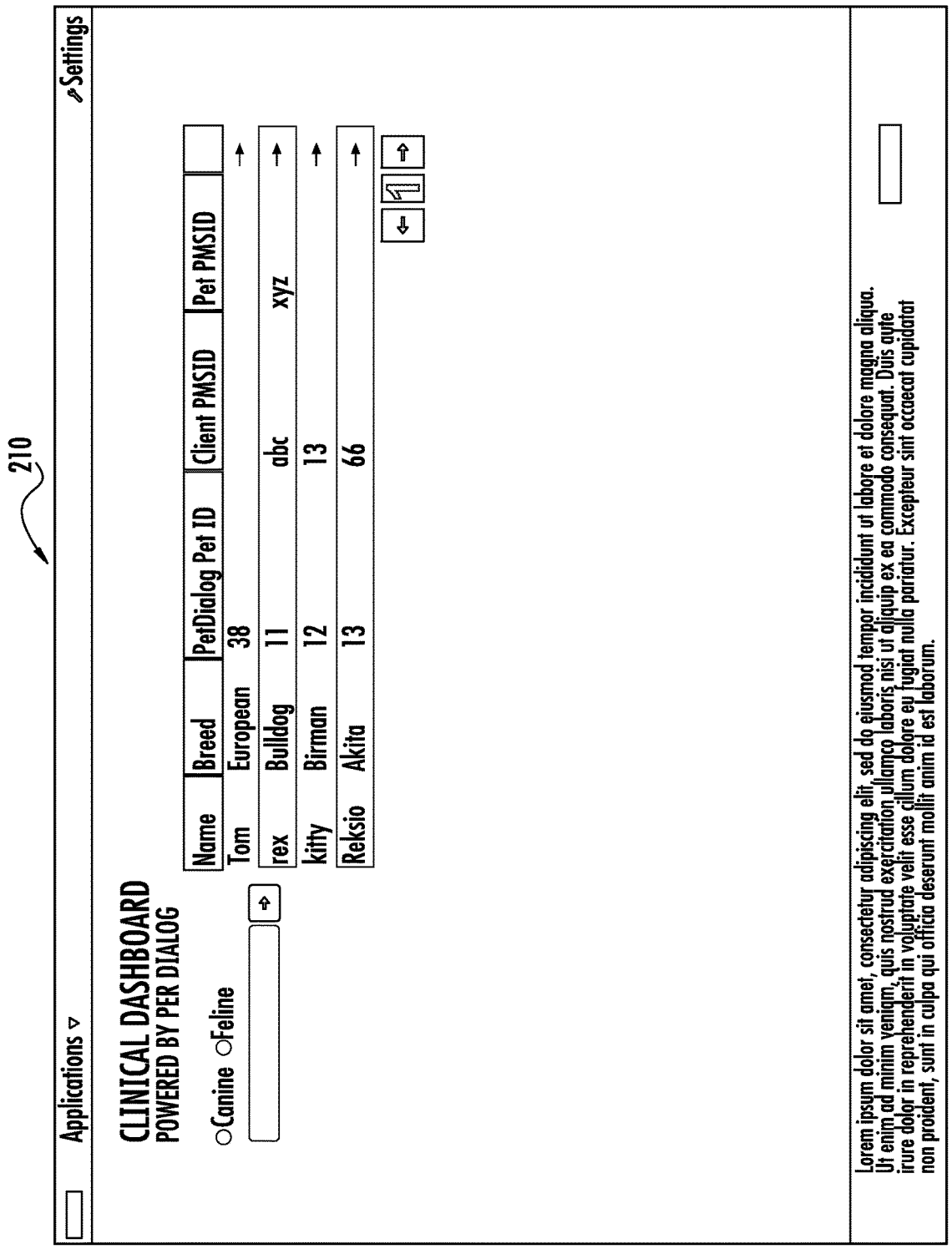

FIG. 6 is a screenshot of a veterinarian interface for viewing a dashboard 210 displaying animal profile information for each animal patient in a veterinarian's practice. The information provided in the dashboard 210 may be an abbreviated or subset of the complete information available in an animal record comprised of animal profile information for each animal. As such, selecting one of the graphical or textual icons presented in the dashboard 210 for a specific animal patient may cause the respective animal record to display, with the entire animal record and animal profile information.

Figure 8:
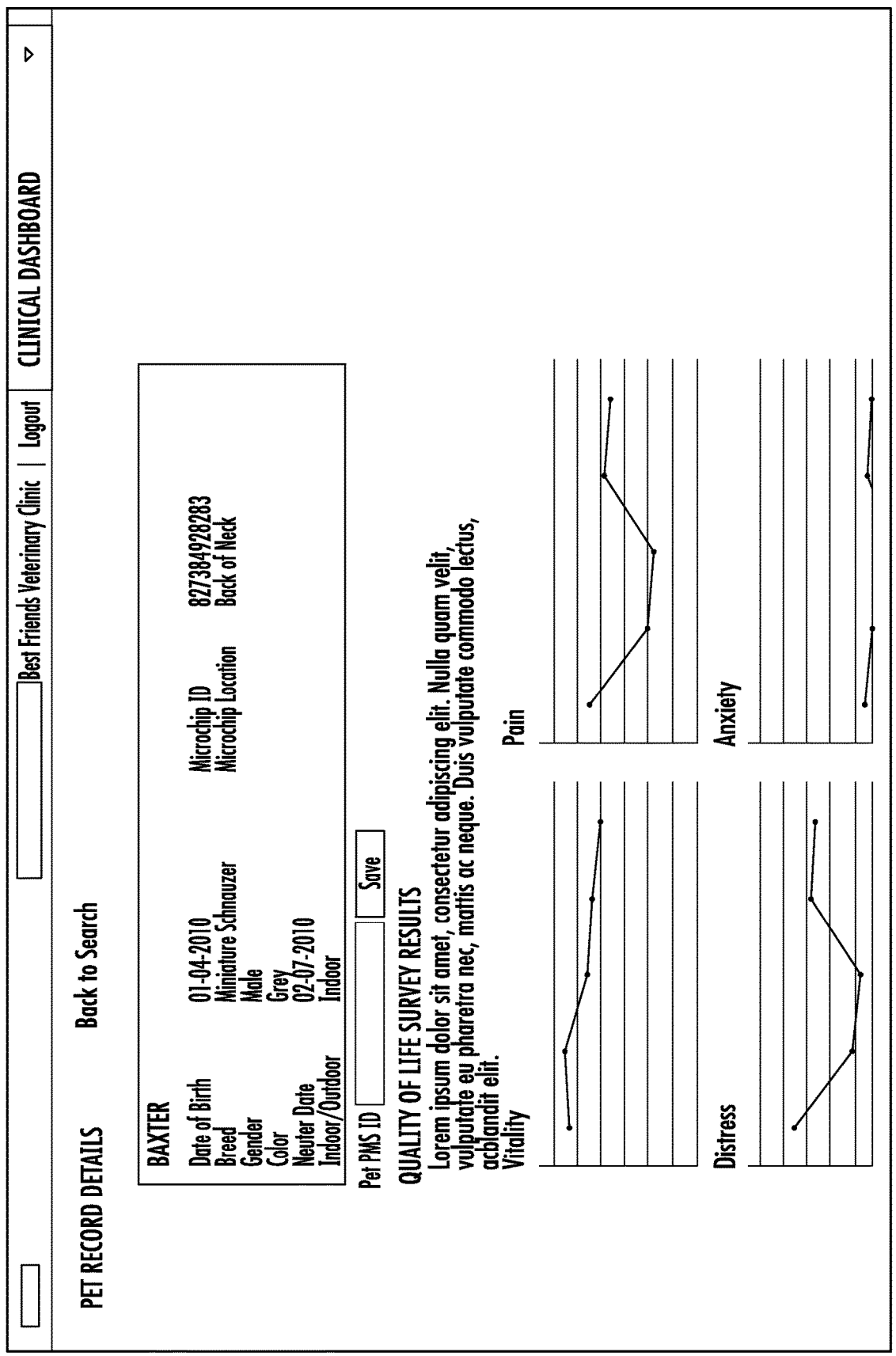

FIGS. 7 and 8 are screenshots of a veterinarian interface displaying an animal record 220 for viewing animal profile information for a respective animal patient in a veterinarian's practice. Animal profile information may be inputted by an animal owner using an animal owner device 104 or by a veterinarian using veterinarian device 102 such that an animal record having a unique identifier is created for a specific animal/patient. Such animal profile information may include, for example, the animal's name, date of birth, species, breed, gender, spayed/neutered status and microchip identification number. The animal record may further include animal wellness information based on data received from the animal and/or the animal owner, as will be described further below.

Figure 9:
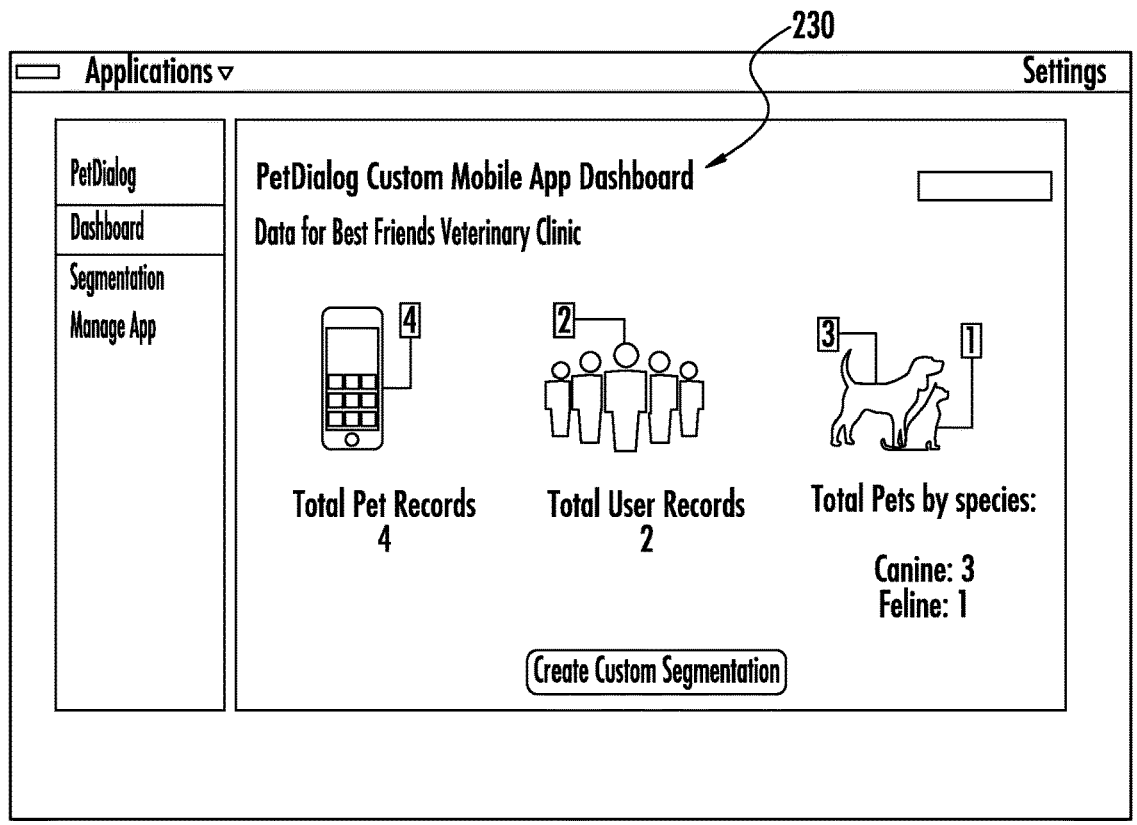

FIGS. 9-12 are screenshots of a veterinarian interface displaying a mobile application module available through the marketing portlet. As shown in FIG. 9, such a mobile application module may include a mobile application dashboard 230 that displays information related to predetermined key performance indicators relevant to a particular business objective or business process. For example, the dashboard

Figure 10:
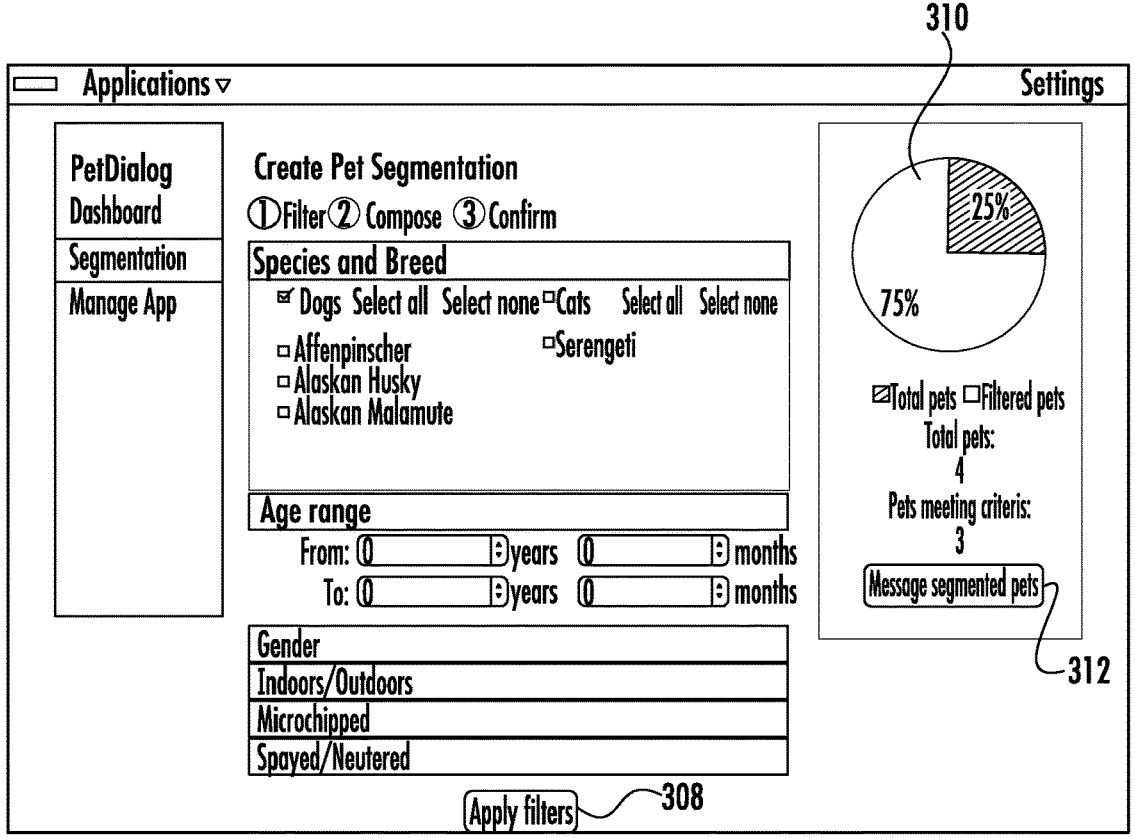

230 may provide information such as, for example, a total number of animal records for a veterinary practice, a total number of users (veterinarians) for a veterinary practice, or segment information of animal patients based on species. Further, as shown in FIG. 10, the mobile application module may include a segmentation or filtering sub-module configured to allow a veterinarian to segment animal patients based on criteria such as species, breed, gender, spayed/neutered status, microchip status, etc. The segmentation sub-module may provide check boxes, drop-down boxes, or other selection mechanisms that allow filtering of the animal record database upon actuation of a filtering icon 308. The veterinarian may then use that segmentation or filtering to send messages directly to animal owner device 104. The veterinarian interface may also display graphical information, such as, for example, pie chart 310, related to the results of the applied segmentation parameters.

Figure 11:
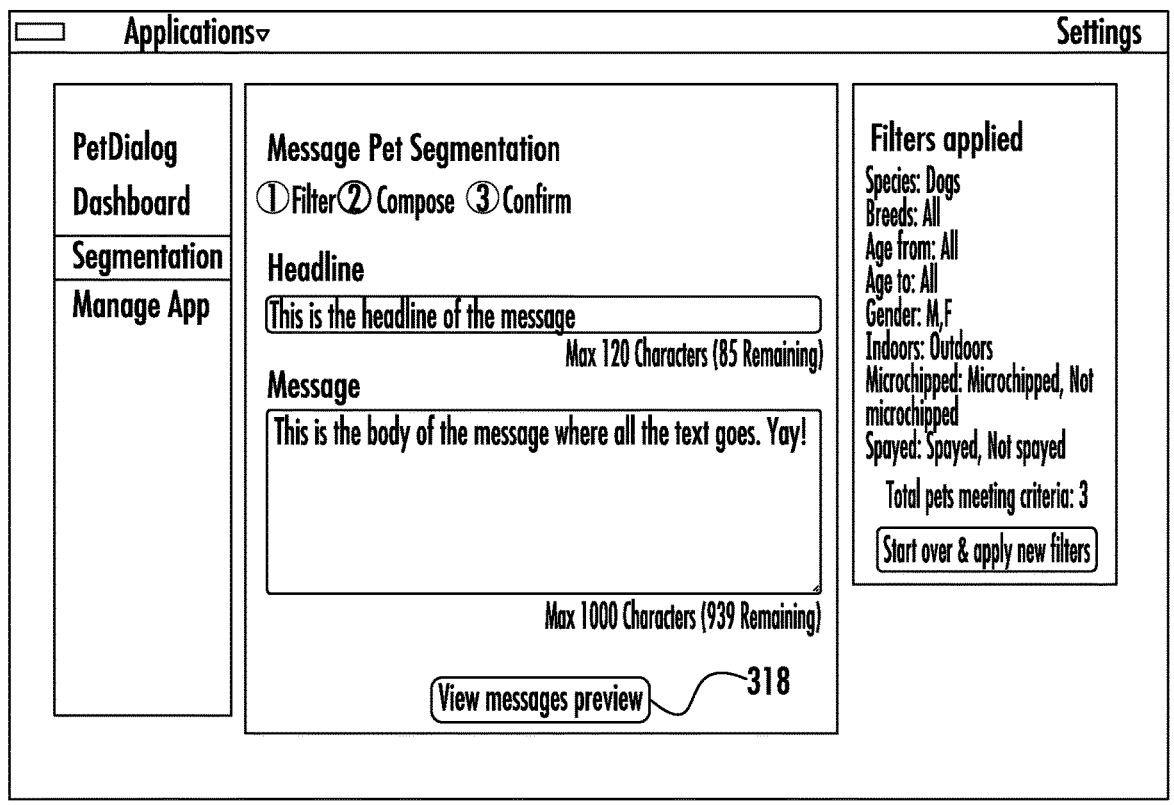
Figure 12:
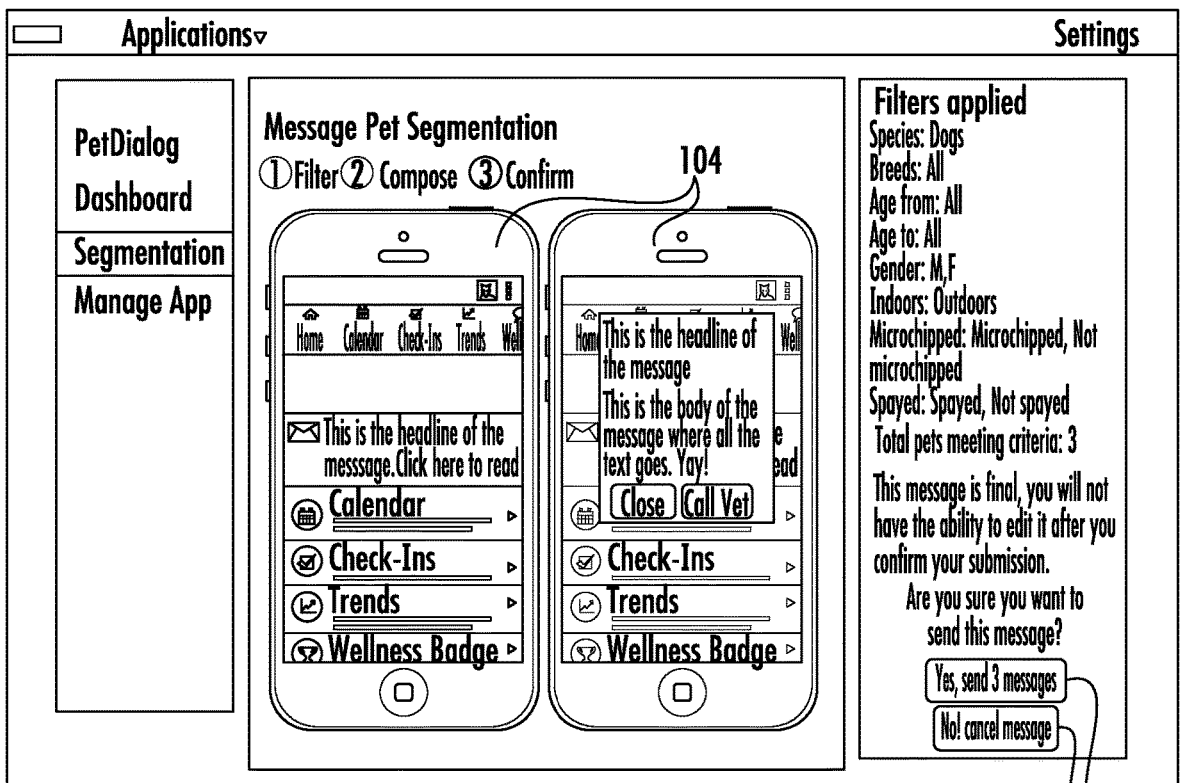

As shown in FIG. 11, based on the filters applied during segmentation of the animal records database, the veterinarian may be presented with a messaging icon 312 (FIG. 10) for accessing a messaging module for composing a textual message that may be sent to the animal owners associated with the segmented animal records. As shown in FIG. 12, upon composing the message, the veterinarian may be requested to confirm or preview the text of the message (via a message preview icon 318) before sending to the desired animal owners. Such confirmation may display the text as will be seen on the animal owner device 104, as well as displaying the applied filters. The veterinarian may be provided with a send icon 314 that is acuatable to send the message to the respective animal owners or selected designees thereof. The veterinarian may also be able to cancel the message by actuating a cancel icon 316.

FIGS. 30 and 31 are screenshots of a veterinarian interface displaying a communications module available through the marketing portlet. As shown in FIGS. 30 and 31, such a communications module may allow veterinarians to customize communications through, for example, email, SMS (text), and the internet. According to some aspects, veterinarians may be able to send alerts, advertisements and other forms of reminders or communications. Hyperlinks to facilitate social media sharing may also be provided. FIG. 32 illustrates an animal owner device 104 displaying information received via SMS from the veterinarian, reminding the animal owner of a vaccination appointment for his or her animal. FIG. 33 illustrates a screenshot of an animal owner device 104 displaying information received via email from the veterinarian, reminding the animal owner of an annual health check for his or her animal. The email reminder message is embedded with video content and graphical indicia for branding of the veterinarian practice sending the information. FIG. 34 illustrates a screenshot of a veterinarian interface displaying a web-based request by an animal owner for a call-back regarding an animal patient.

FIGS. 35-37 are wireframes of a veterinarian interface displaying a practice support module available through the business portlet. As shown in FIG. 35, such a practice support module may include a business performance dashboard 250 that displays information related to predetermined key performance indicators relevant to a particular business objective or business process. For example, such key performance indicators may include actual growth of the business, growth percentage of the business, or actual value of the business. According to some aspects, certain benchmarks may be provided for filtering such that the veterinary practice may be compared to other practices of similar size, location, and geography. The business performance dashboard may help veterinarians understand the performance of their clinics. Such information may be made available in analytics tools. FIG. 36 illustrates a wireframe displaying reportable content available to the veterinarian. In this regard, the veterinarian may be able to generate customized or standard reports related to various aspects of the veterinary practice or business. Filtering options may be available such that the veterinarian can customize the reports to his or her liking. Such reports may include graphical and/or textual information, and may be downloadable, printable, or otherwise made available to the veterinarian. FIG. 37 illustrates a wireframe displaying text boxes 320 for inputting information related to the veterinary practice and/or for establishing a record related to the veterinary practice.

FIG. 38 is a screenshot of veterinarian interface displaying a practice support module available through the business portlet. The screenshot illustrates a report generating sub-module that may allow the veterinarian to generate various reports related to, for example, client or staff turnover, clients, consultations, or prevention. The reports may be segmented for customization using filters such as species, timeframe, productivity, key performance indicators, report type, and other benchmarking parameters such as geography, location, and practice size. Dropdown boxes may be utilized to apply filters for generating the desired report(s). The reports may also provide information related to key performance indicators. While the reports may be displayed on the veterinarian interface, the reports may also be downloadable, printable, etc. by actuating appropriate icons. Such reporting information may be provided to the veterinarian as a textual or graphical representation.

A human resources module may be provided and accessible through the staff portlet. The human resources module may allow veterinarians to manage their staff performance, review, and other human resources functions.

As previously mentioned, the veterinary practice support system may receive information and/or data related to animal wellness for an animal patient serviced by the veterinary practice. Such animal wellness information or data may originate from the animal owner via animal owner device 104, wherein such information/data is transmitted over electronic network 100 to veterinarian application program 112 such that the information is available to the veterinarian via veterinarian device 102 in, for example, the animal record or the marketing or clinical portlets. The information or data may be inputted by the animal owner using animal owner device 104 implementing a computer program product such as, for example, a mobile application. In addition, animal device 101 may be worn by the animal such that data is transmitted from animal device 101 to animal owner device 104 and/or veterinarian device 102, over electronic network 100.

In one exemplary aspect of the present disclosure, the animal owner may have a mobile application available on animal owner device 104 (e.g., smartphone), wherein the mobile application is capable of capturing information related to the subject animal. For example, as shown in FIG. 13, the mobile application may have several application modules and associated actuatable icons 400 for implementing such modules. The individual modules may allow various information related to the subject animal to be input such that the information can be transmitted across electronic network 100. For example, the modules may be related to flea and tick treatment, worming appointments, medication reminders, animal record information, time spent socializing, calendar, check-up appointments, weight check-ins, food and treat tracking, walk time and distance tracking, health assessments, trends and patterns (analysis), veterinarian information, play activities and quality time. Advantageously, this animal wellness data collected by the animal owner may be shared with the veterinarian over electronic network 100. In this regard, the veterinarian may be able to track wellness information of the animal patient. This is extremely beneficial to providing improved care for the animal patient. The data sent to the veterinarian may be analyzed or manipulated to provide information in a way that can improve care for the animal patient. In this manner, the animal owner may collect and input information related to the wellness of the subject animal such that the information and data can be shared with the veterinary practice support system over electronic network 100, to allow the veterinarian to track wellness of the subject animal. Further, the veterinarian may review this information through the veterinary practice support system when the animal patient visits for a check-up, vaccination, or sick visit. To that end, the veterinarian may have available a wealth of information for treating the animal patient.

Figure 17:
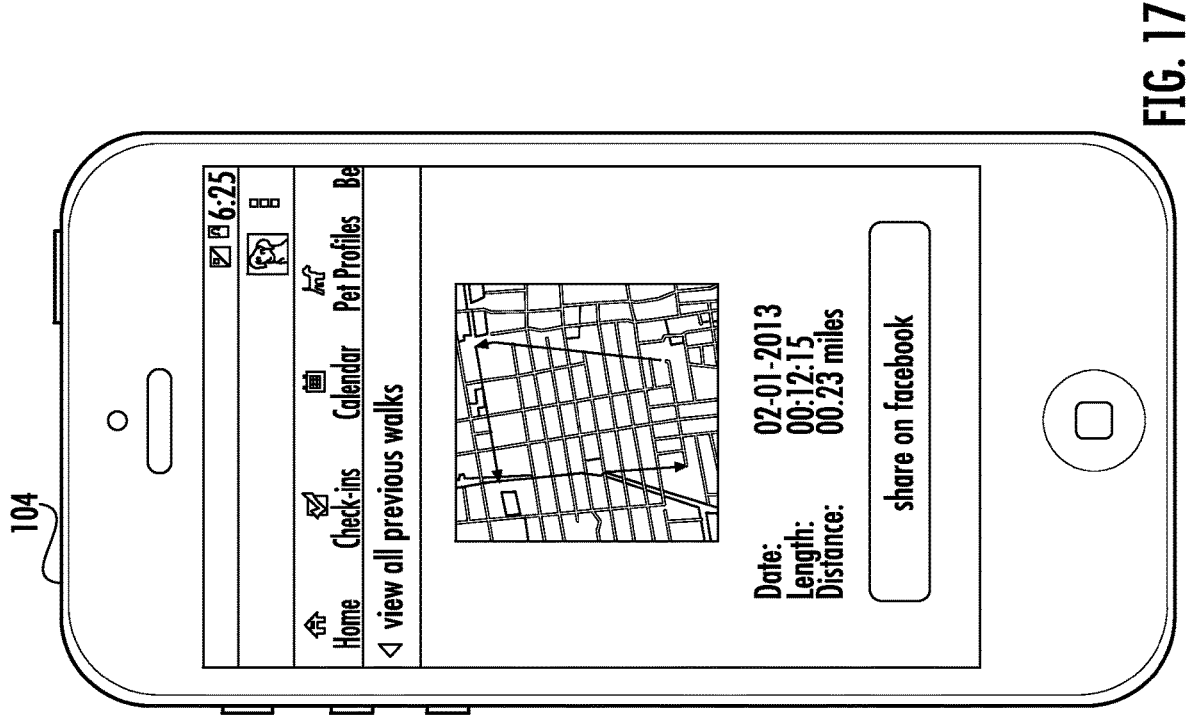
Figure 19:
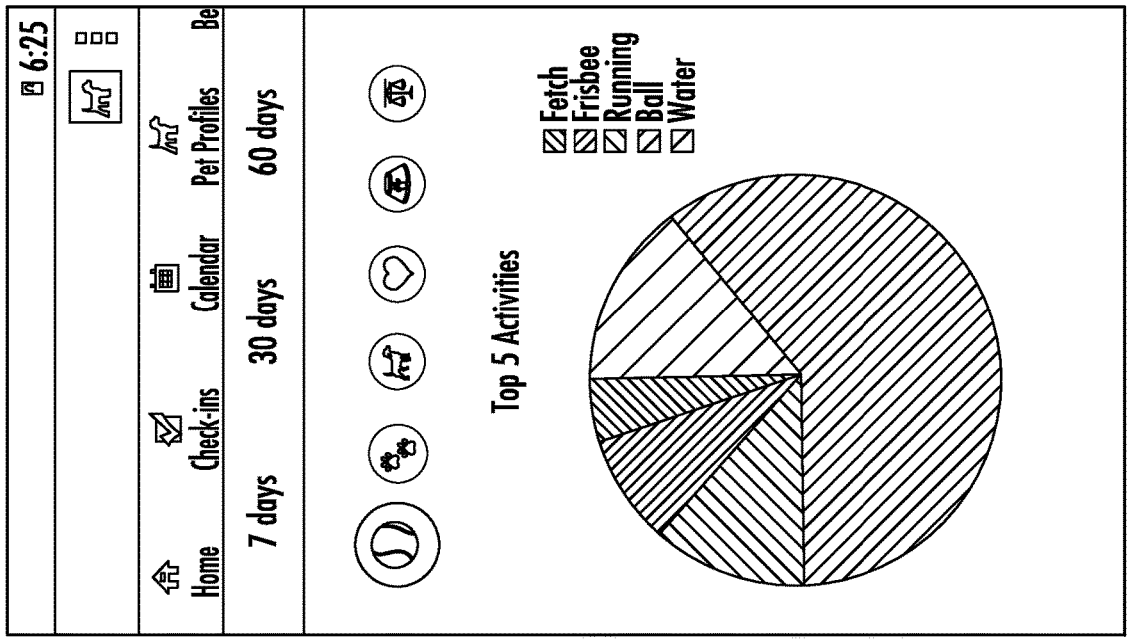
Figure 18:
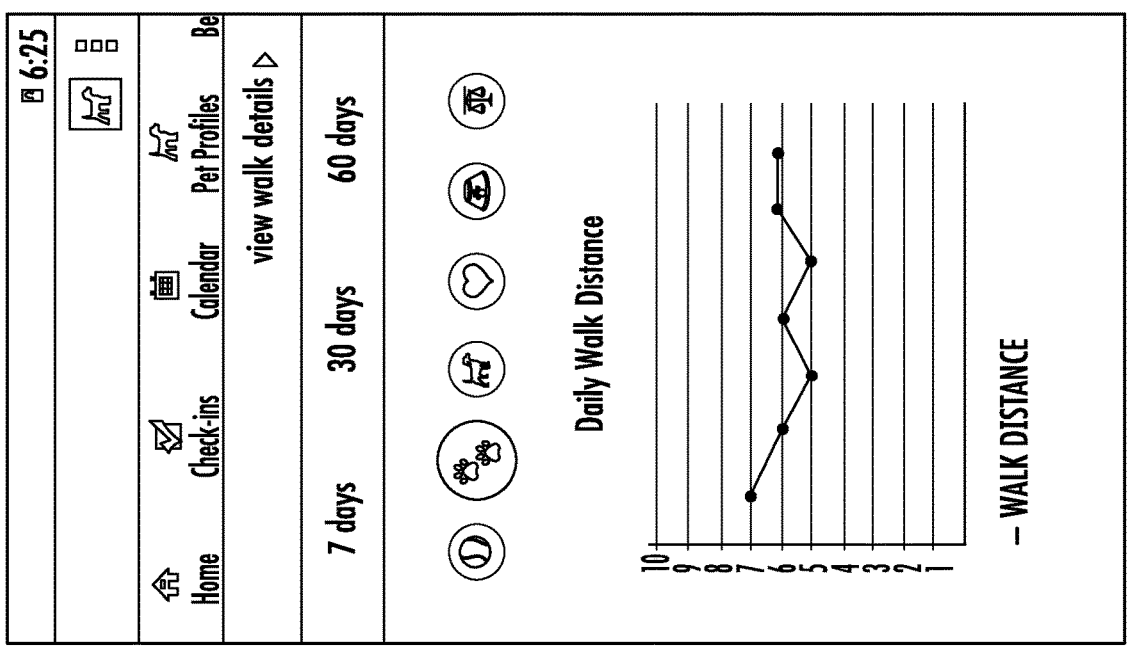
Figure 20:
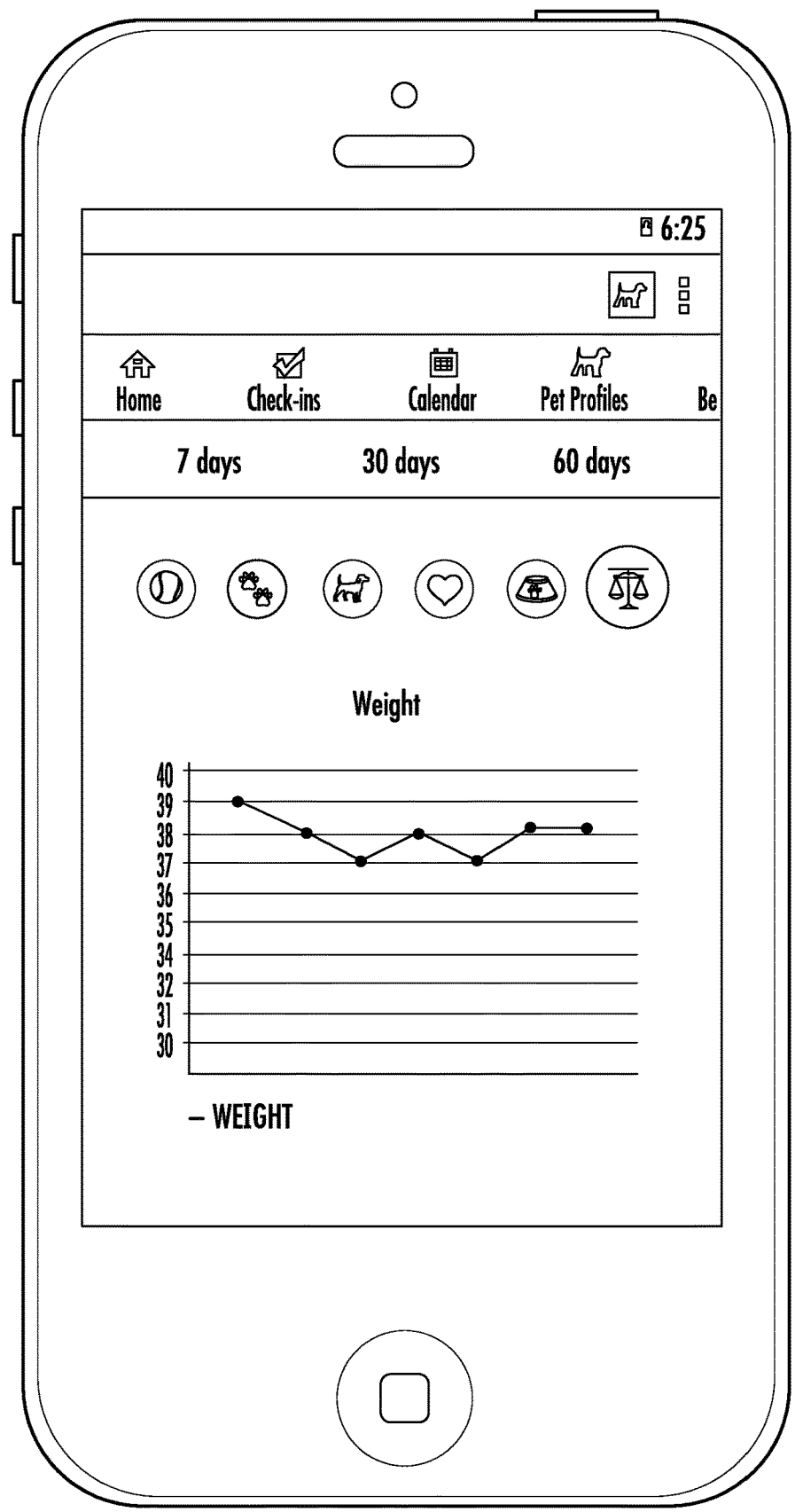
Figure 23:
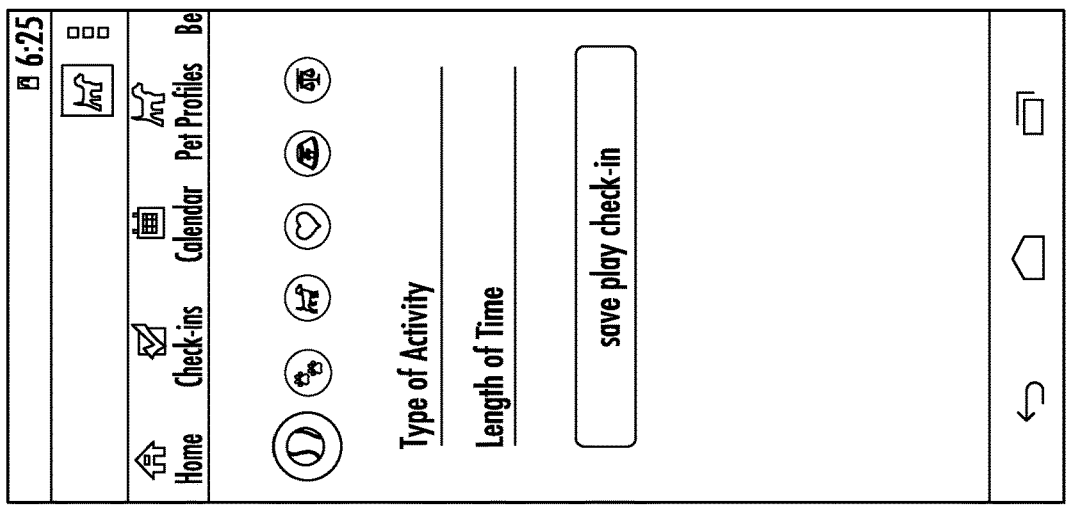
Figure 22:
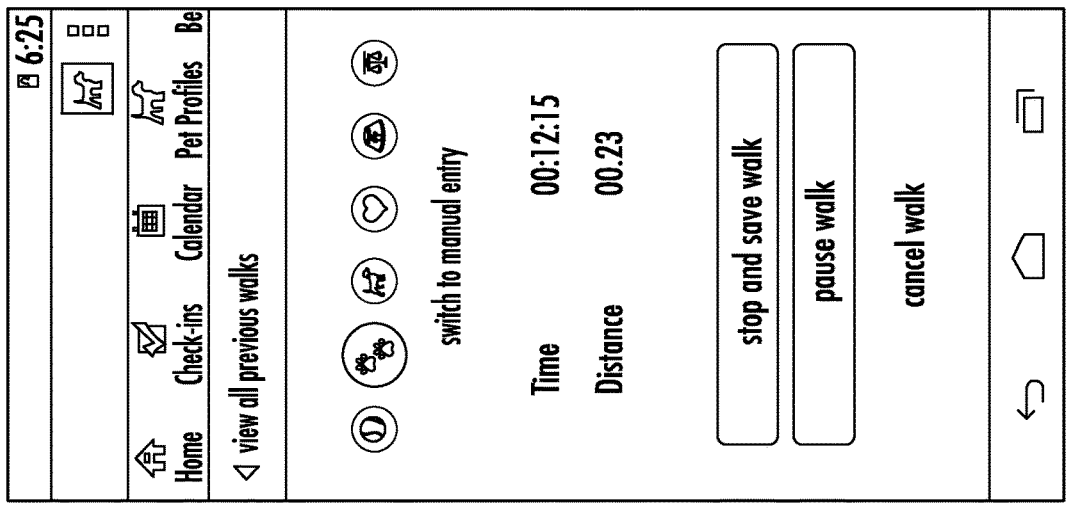
Figure 21:
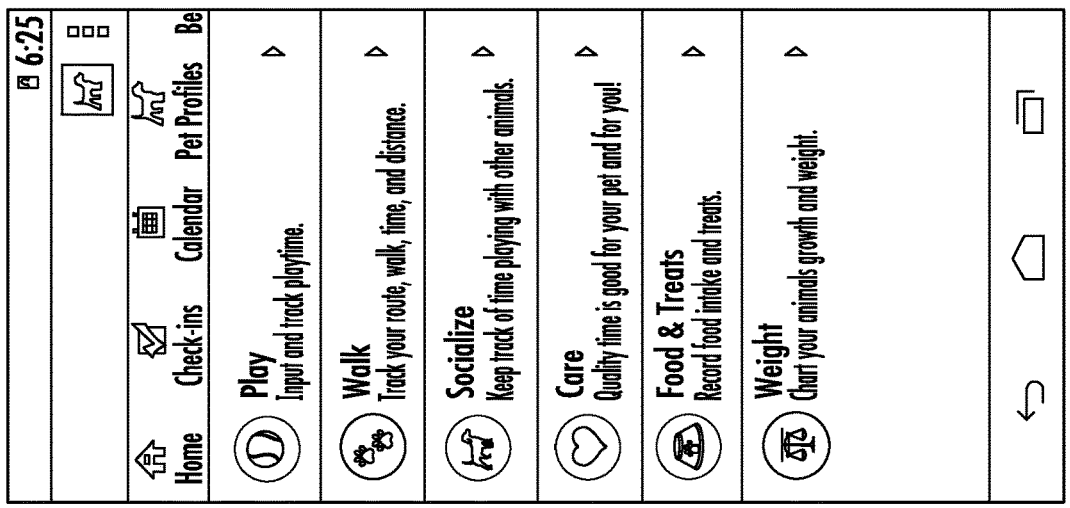
Figure 26:
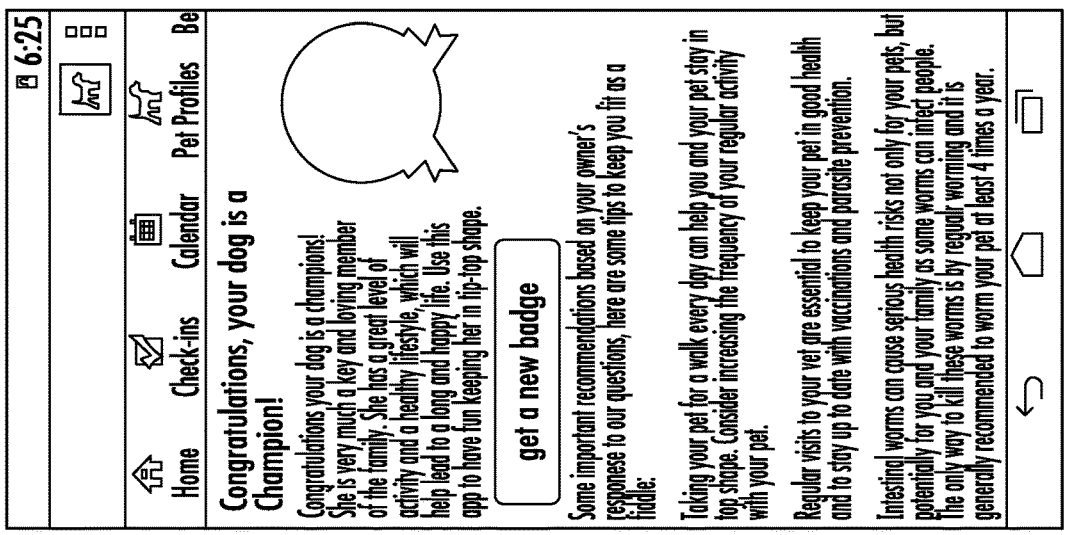
Figure 25:
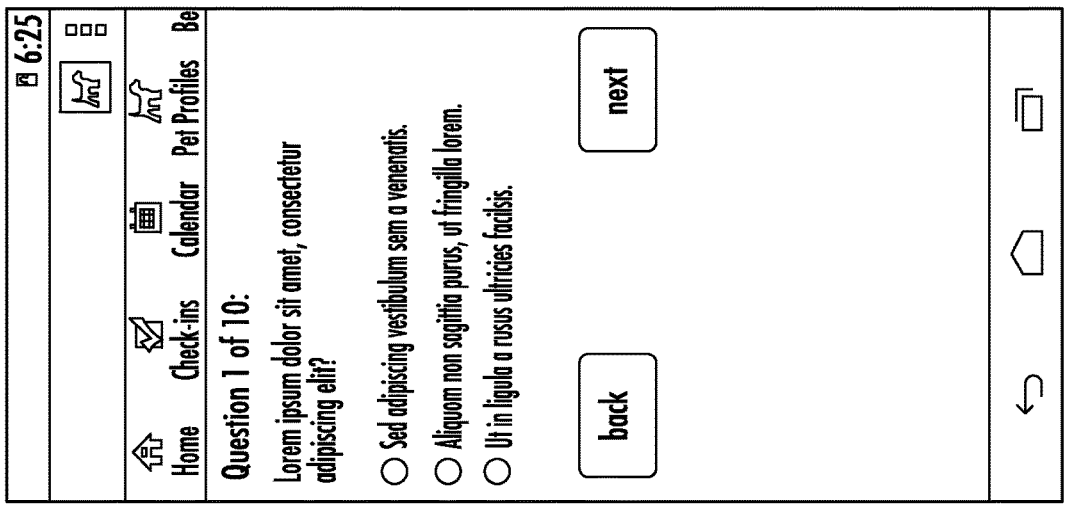
Figure 24:
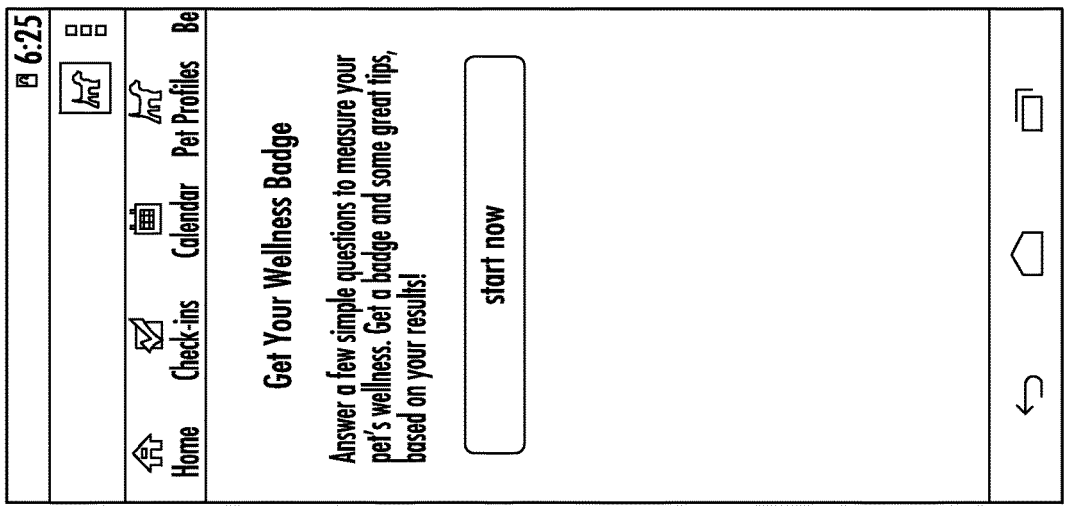
Figure 29:
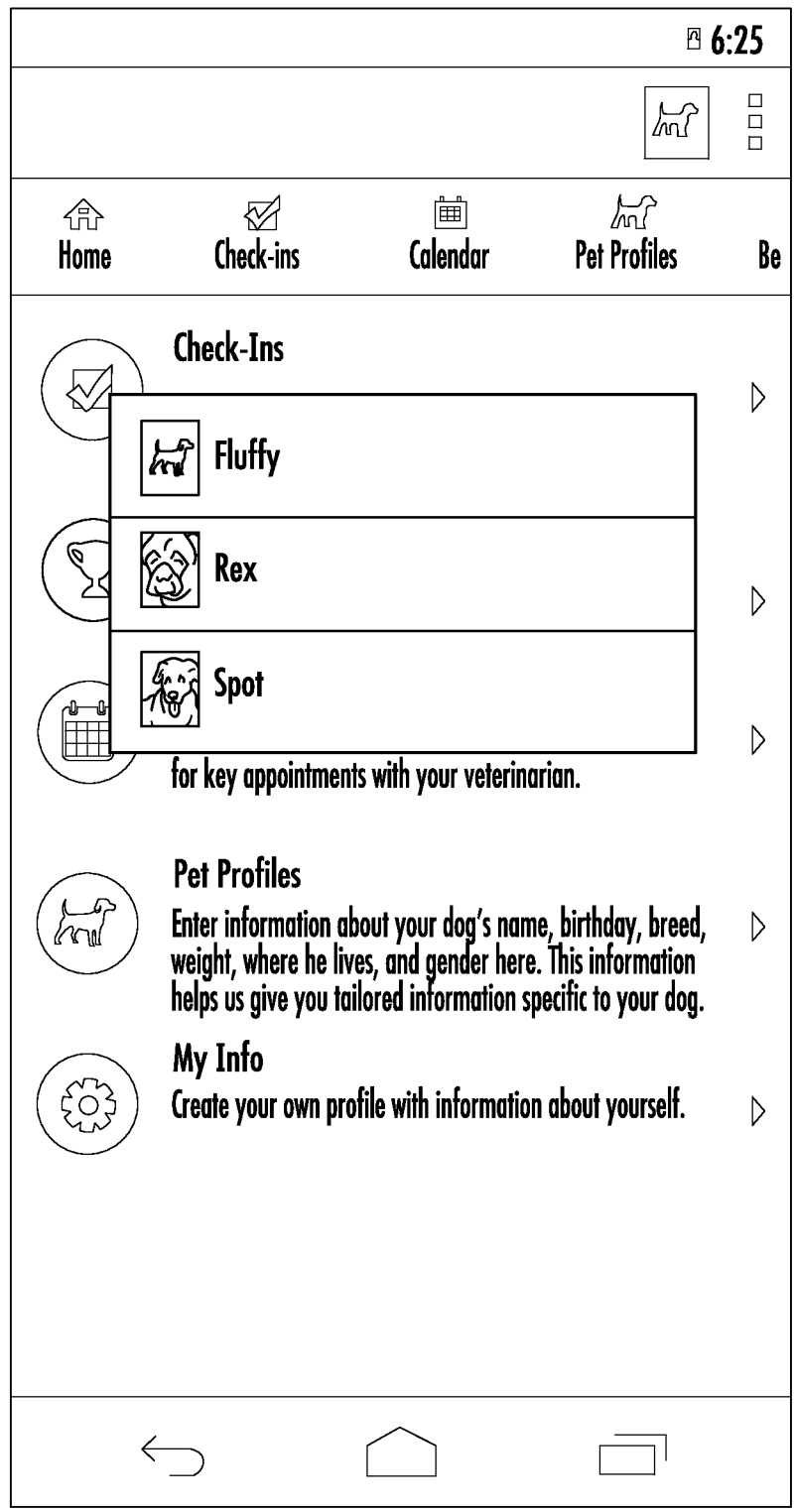

FIGS. 14-29 are various screenshots of various aspects of a mobile application available on animal owner device 104. For example, FIG. 16 depicts a display of time and distance data collected during a walk by the animal owner with the subject animal. FIG. 17 depicts a map display of the route taken by the subject animal. FIGS. 18-20 illustrate the display of data analytics as based on information inputted into the mobile application modules. For example, FIG. 18 graphically displays daily walking distance over a period of time; FIG. 19 graphically displays the activities of the animal; and FIG. 20 graphically displays change in weight of the subject animal over a period of time.

In some instances, the data provided to the veterinarian may be based on quality of life information provided through a survey completed by the animal owner. The survey may be in the form of a questionnaire, wherein the answers provided are processed and analyzed to provide the results in the form of a quality of life score that may be reviewed by the veterinarian. Such results may include information related to vitality, pain, distress and axiety, as fluctuating over a designated period of time. The quality of life results may be depicted in graphical form, as shown in FIG. 8.

Referring now to the enclosed figures, FIG. 1 is a schematic diagram of a system and environment for collecting, processing, and displaying animal wellness data, according to an exemplary embodiment of the present disclosure. As shown in FIG. 1, the system and environment may include a plurality of veterinarian devices 102 and animal owner devices 104 disposed in communication with an electronic network 100. Electronic network 100 may be the Internet, or any other combination of wired and/or wireless electronic networks.

In one embodiment, each of veterinarian devices 102 may include a server, personal computer, tablet computer, mobile device, smartphone, and/or personal digital assistant ("PDA") disposed in communication with electronic network 100. For example, in one embodiment, each of veterinarian devices 102 may be a touchscreen enabled device, such as an Apple iPad, Samsung Galaxy, Amazon Kindle, Microsoft Surface, or any other equivalent or similar device. Each of veterinarian devices 102 may have a web browser or mobile browser installed for receiving and displaying content from web servers. Thus, each of veterinarian devices 102 may be configured to receive and display data that is received and processed from animal owner devices 104, over electronic network 100.

In one embodiment, each of animal owner devices 104 may include a server, personal computer, tablet computer, mobile device, smartphone, and/or personal digital assistant ("PDA") disposed in communication with electronic network 100. For example, in one embodiment, each of animal owner devices devices 104 may be a touchscreen enabled device, such as an Apple iPad, Samsung Galaxy, Amazon Kindle, Microsoft Surface, or any other equivalent or similar device. Each of animal owner devices 104 may have a web browser or mobile browser installed for receiving and displaying content from web servers. Thus, each of animal owner devices 104 may be configured to input and transmit data to veterinarian devices 102, over electronic network 100.

The system and environment may further include a animal device 101 disposed in communication with electronic network 100. The animal device 101 may include a combination of wellness sensors, a memory, a battery, and/or a transceiver, one or more of which may be disposed within or in communication with animal owner devices 104. In one embodiment, an accelerometer may be disposed in short-range wireless, Bluetooth, radio-frequency (RFID), and/or near-field communications (NFC) communication with animal owner device 104 such as a mobile device carried or worn by the animal owner. Animal device 101 may be connected to electronic network 100 through a cellular network and/or a Wi-Fi network. Thus, animal device 101 may be configured to collect wellness data from a animal, and transmit collected wellness data over electronic network 100.

As shown in FIG. 1, a plurality of server systems 106, a browser web server 114, and/or a mobile web server 116 may also be disposed in communication with electronic network 100. In one embodiment, server systems 106 may be configured to receive wellness data from animal owner devices 104 over electronic network 100. Any of the devices or functionality of server systems 106, browser web server 114, and/or a mobile web server 116 may be combined together or separated, and may be operated by a single administrative entity, or outsourced to one or more other entities, such as a web hosting entity, web storage entity, and/or cloud computing service.

As shown in the embodiment of FIG. 1, server systems 106 may include a animal wellness data analyzer 110, which may be configured to perform analysis on received animal wellness data. Specifically, animal wellness data analyzer 110 may be configured to analyze received animal wellness data for tracking, for example, food activity, play activity, love activity, socialize activity, walk activity or weight activity, as will be described in more detail below. This data may be analyzed based on, for example, food consumed, duration of activity, duration of encounter, distance tracked, or weight.

Server systems 106 may also include one or more databases 108, where animal wellness data analyzer 110 may be configured to store the received animal wellness data. Any received data may be stored in the databases 108 in an encrypted form to increase security of the data against unauthorized access.

Server systems 106 may also include a veterinarian application program 112 that allows a veterinarian to control parameters of the system, such as threshold values used by the animal wellness data analyzer 110 in performing analyses. The veterinarian application program 112 also displays data to the veterinarian and allows the veterinarian to select types of data to display, time periods of the data to display, levels of data detail to display and other operating parameters of the system. For example, the veterinarian may select a beginning and ending time surrounding tracked activity. In response to a query by the veterinarian, the veterinarian application program 112 may fetch and display data from the databases 108. If the requested data is not available in the databases 108, or if the requested data is not available in the database 108 at the level of detail requested by the veterinarian, the veterinarian application program 112 may automatically communicate with the transceiver of an animal owner device 104 to fetch the appropriate data in the appropriate amount of detail.

The veterinarian application program 112 may implement appropriate security protocols, such as requiring the veterinarian to enter logon credentials, so as to appropriately limit access to animal wellness data.

As shown in FIG. 1, server systems 106 may be disposed in communication with a browser web server 114 and/or a mobile web server 116. Each of browser web server 114 and/or mobile web server 116 may be configured to interact with veterinarian devices 102, such as to accept user (veterinarian or administrator) inputs and generate appropriate displays to facilitate user interaction with the veterinarian application program 112. For example, browser web server 114 and/or mobile web server 116 may be configured to generate a window-metaphor based computer user interface on a screen of veterinarian device(s) 102 or screen coupled to the remote server systems 106, or the browser web server 114 and/or mobile web server 116 may generate web pages that are rendered by a browser or application of the veterinarian devices 102. The veterinarian devices 102 and the browser web server 114 and/or mobile web server 116 may communicate with each other using an appropriate encrypted protocol, such as Hypertext Transfer Protocol Secure (HTTPS).

A method for collecting, processing, and displaying animal wellness data, e.g., using the exemplary system and devices of FIG. 1 is also provided, according to an exemplary embodiment of the present disclosure. The method may initially include receiving animal wellness data from one or more animal owners. For example, server systems 106 may receive animal wellness data from one or more animal owner devices 104, which may then be stored in databases 108.

Figure 14:
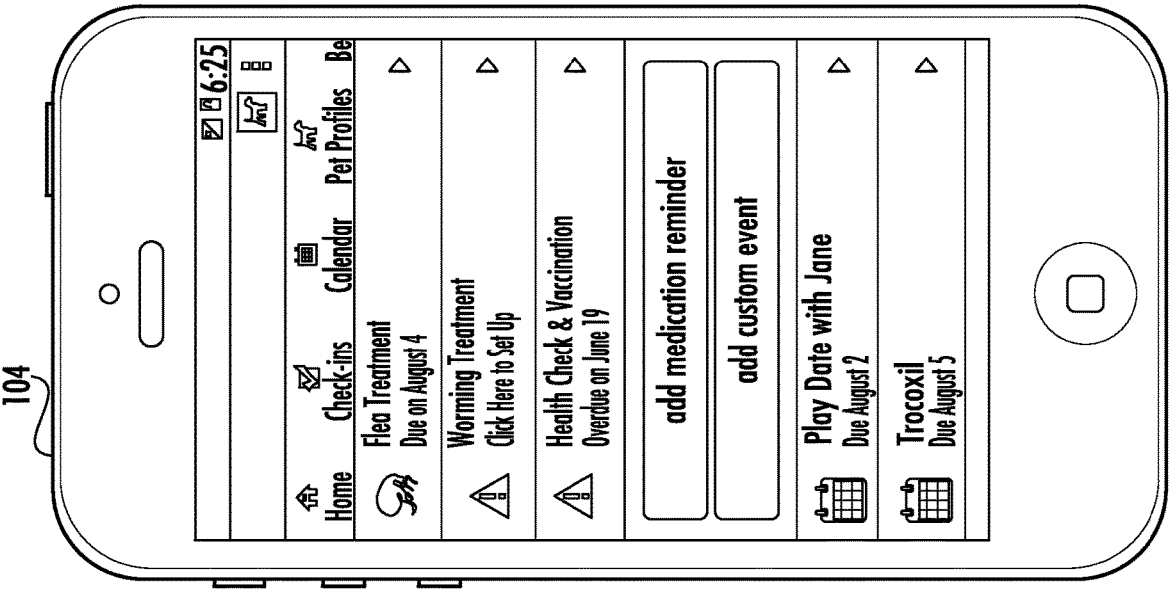
Figure 15:
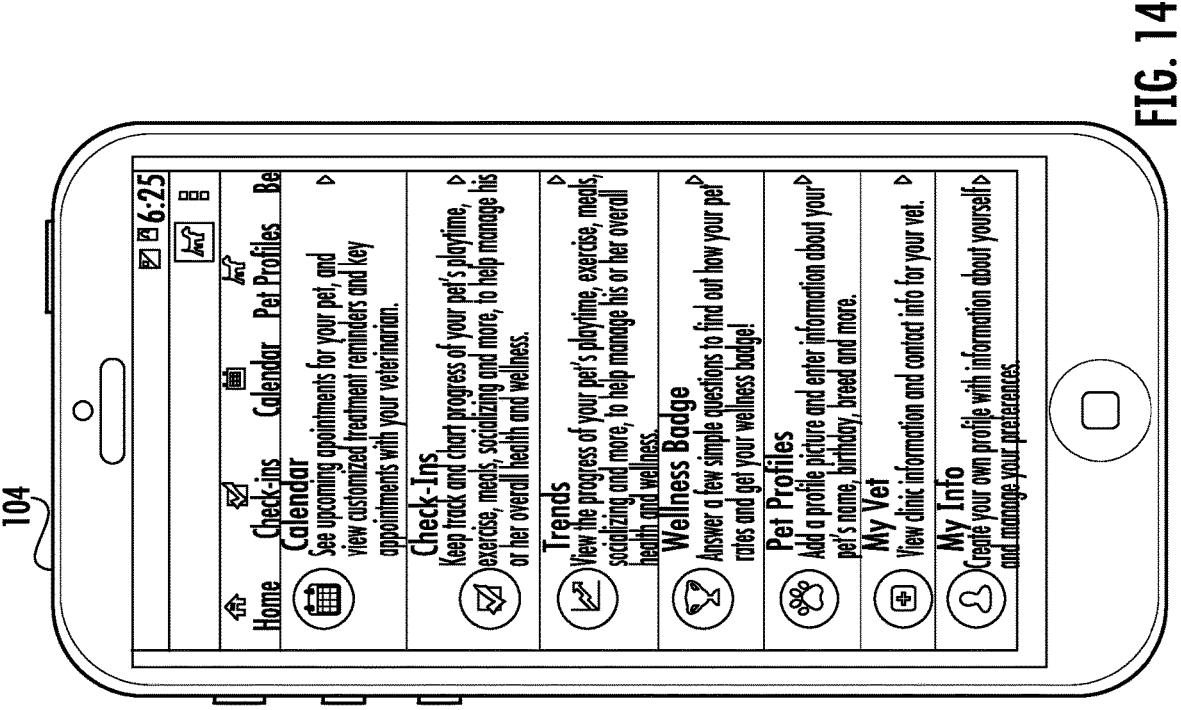
Figure 16:
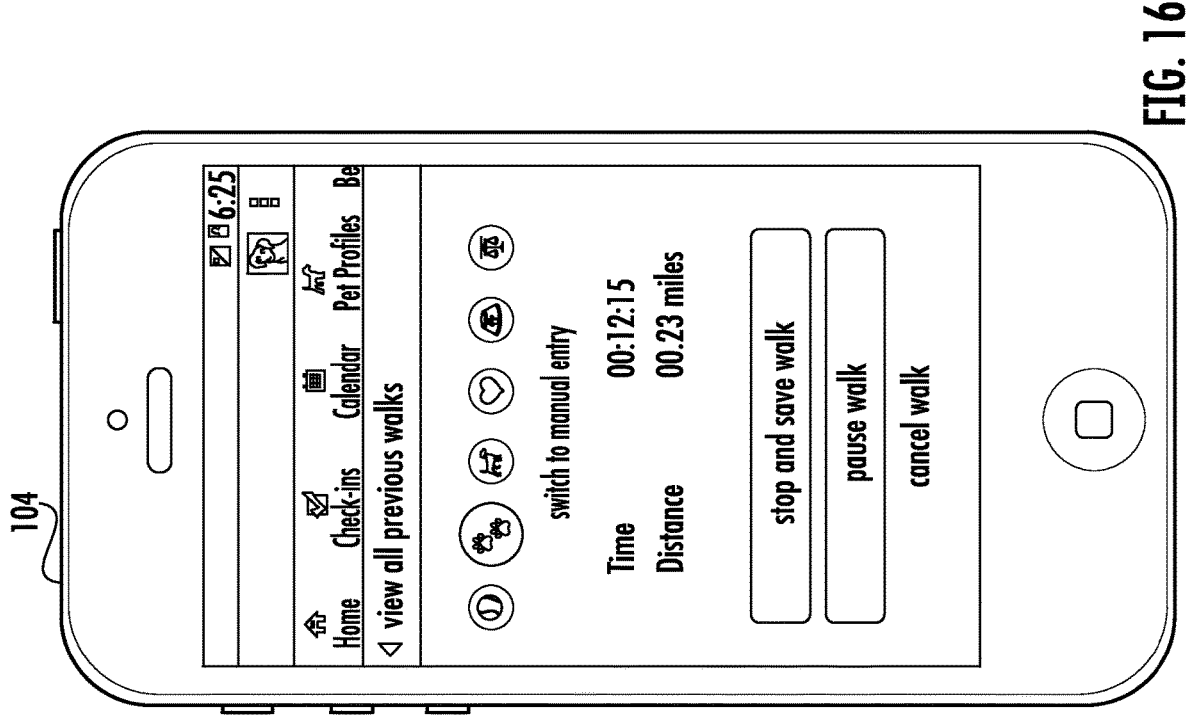

FIGS. 14 and 15 illustrate an animal owner device 104 for collecting animal wellness data, according to an exemplary aspect of the present disclosure. Thus, as discussed above, animal owner devices 104 may be configured to collect animal wellness data, store the collected data in a memory, and send a full detail or less-detailed version of the data to the remote server systems 106 for storage in databases 108.

The processing of the animal wellness data may also include filtering animals based on the animal profile information provided in the animal record, such as species, breed, etc. The method may further include, either concurrently with or asynchronously from processing the animal wellness data, receiving a request for animal wellness data from a veterinarian. For example, a veterinarian may use a browser or other software installed on a veterinarian device 102 to generate a request for animal wellness data from browser web server 114, mobile web server 116, and/or server systems 106. The veterinarian may generate the request by simply manipulating a user interface, such as touching a user element associated with an animal for whom the veterinarian desires to review animal wellness data. Alternatively, the veterinarian may request animal wellness data for all of the veterinarian's animal patients, or all of the animal patients of the veterinarian's practice. The method may also include modifying a display of animal wellness data based on received veterinarian input.

In one aspect, the veterinarian interface may display, for each animal patient, how long the animal patient has been monitored by a animal owner device 104 or animal device 101. For example, the veterinarian interface may display a number of days or weeks associated with each animal patient, reflecting the number of days or weeks the animal patient has worn or been monitored by the device 104 or 101. In one aspect, the veterinarian interface may sort or categorize a display of animal patients based on the number of days or weeks the animal patient has worn or been monitored by the device 104 or 106.

In addition, the veterinarian interface may indicate an activity level associated with each animal patient. For example, each animal owner device 104 or animal device 101 may contain a GPS device, an accelerometer, and/or any other device that generates location, movement, or activity level data associated with a user. System 106 may process such received data to generate an activity level to be associated with the animal patient. The activity level may be a range, (e.g., low, medium, high), a percentage of prescribed or maximum activity, a numerical value associated with activity (e.g., a ranking or moving average), or a time amount associated with the activity (e.g., active for x of the past y hours). The veterinarian interface may then sort or categorize a display of animal patients based on an activity level determined for each animal patient. Thus, a veterinarian may easily view the veterinarian interface to determine relative or absolute activity levels of his or her animal patients to provide a better understanding of their general health status or wellness. In one embodiment, system 106 may generate alerts for sending to veterinarians when an animal patient's activity level reaches a certain high or low threshold.

In addition, interface 800 may indicate whether a animal patient is complying with a prescribed medication, treatment, activity, or other regimen. For example, system 106 may track each animal patient's compliance with a prescribed regimen, e.g., through accelerometers or any other biocompatible sensors. System 106 may then determine whether an animal patient is complying with a veterinarian-prescribed regimen, and if desired, generate one or more alerts for sending to a veterinarian when an animal patient is not in compliance with its prescribed regimen. For example, system 106 may alert a veterinarian when an animal owner is not following a prescribed drug treatment program, diet program and/or exercise program for the animal patient. It should be appreciated that the above-discussed indicia and related functionality (e.g., medical device battery level/signal, patient device monitoring period, patient activity level, patient compliance, etc.) may be incorporated into any of the veterinarian interfaces described in the present disclosure.

FIGS. 7 and 8 are screenshots of a veterinarian interface for reviewing animal patient data, according to an exemplary aspect of the present disclosure. Specifically, FIGS. 7 and 8 depict an interface that provides a detailed view of a veterinarian interface for reviewing an animal patient's data. The veterinarian may switch from a detailed view of one animal patient to a detailed view of another animal patient by tapping, swiping, or otherwise selecting one of the other animal patients displayed in interface.

A remote animal health monitoring system may include a processor controlled by instructions stored in a memory. For example, the transceiver assembly may include and be controlled by such a processor, and the remote server may be controlled by another such processor. The memory may be random access memory (RAM), read-only memory (ROM), flash memory or any other memory, or combination thereof, suitable for storing control software or other instructions and data.

Some of the functions performed by the remote animal health monitoring system have been described with reference to flowcharts and/or block diagrams. Those skilled in the art should readily appreciate that functions, operations, decisions, etc. of all or a portion of each block, or a combination of blocks, of the flowcharts or block diagrams may be implemented as computer program instructions, software, hardware, firmware or combinations thereof.

Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer network.

In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

Many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. A system for supporting a veterinary practice, the system comprising:

an electronic network;

an animal device worn by an animal and in communication with the electronic network, the animal device having a biocompatible sensor, and the animal device being configured to collect wellness data from an animal and transmit the collected wellness data over the electronic network, the wellness data being related to compliance with a veterinarian-prescribed regimen of a prescribed medication for the animal;

at least one veterinarian device in communication with the electronic network, the veterinarian device being configured to receive and display the wellness data received or processed over the electronic network;

a processor in communication with the electronic network and controlled by a plurality of computer executable instructions stored in a memory, the memory being in communication with the processor;

an animal owner device in communication with the electronic network and configured to send wellness data to the processor;

a display device in communication with the processor;

a graphical user interface generated by the processor for display at the display device in response to the execution of the plurality of instructions by the processor;

a plurality of acuatable icons displayed as part of the graphical user interface, the actuatable icons being associated with a plurality of business-related functions for operating a veterinary practice, each icon being actuatable to access an associated portlet and display additional information associated with the respective function of a veterinary practice on the graphical user interface;

an animal segmentation module configured to filter and segment a plurality of individual animal records from an animal records database housing animal wellness data received from animal owner devices;

a messaging module configured to compose and send a message to the animal owner device based on the segmented animal records; and wherein the processor is configured to generate and send an alert to the at least one veterinarian device when the animal is not in compliance with the veterinarian-prescribed regimen of the prescribed medication for the animal.

2. A system according to claim 1, wherein the icons include a business category icon, a clinical-related information icon, a marketing-related information icon, and a staff-related information icon.

3. A system according to claim 1, wherein one of the icons is configured to be visually-distinguished from the other icons upon actuation.

4. A system according to claim 1, further comprising a dashboard configured to provide key performance indicators of the veterinary practice.

5. A system according to claim 3, wherein the dashboard includes at least one graphical indicia or representation for displaying key performance indicator information.

* * * * *